US009358569B2

(12) United States Patent
Burt et al.

(10) Patent No.: US 9,358,569 B2
(45) Date of Patent: Jun. 7, 2016

(54) ULTRASONIC SURFACE TREATMENT DEVICE AND METHOD

(75) Inventors: Diane Joyce Burt, New Windsor, NY (US); John Aubrey Creek, Bridgewater, NJ (US); Christopher Michael Evans, Montvale, NJ (US); Benjamin David Hindle, Ridgewood, NJ (US)

(73) Assignee: Reckitt Benckiser LLC, Parsippany, NJ (US)

(*) Notice: Subject to any disclaimer, the term of this patent is extended or adjusted under 35 U.S.C. 154(b) by 621 days.

(21) Appl. No.: 13/509,654

(22) PCT Filed: Nov. 16, 2010

(86) PCT No.: PCT/GB2010/002098
§ 371 (c)(1), (2), (4) Date: Dec. 14, 2012

(87) PCT Pub. No.: WO2011/061479
PCT Pub. Date: May 26, 2011

(65) Prior Publication Data

US 2013/0079732 A1 Mar. 28, 2013

Related U.S. Application Data

(60) Provisional application No. 61/262,402, filed on Nov. 18, 2009.

(51) Int. Cl.

| | |
|---|---|
| *B05B 17/06* | (2006.01) |
| *B05B 17/00* | (2006.01) |
| *B05B 7/00* | (2006.01) |

(Continued)

(52) U.S. Cl.
CPC .......... *B05B 17/0646* (2013.01); *A61M 35/003* (2013.01); *B05B 7/0012* (2013.01); *B05B 15/00* (2013.01); *B05B 17/0607* (2013.01); *B05B 17/0615* (2013.01); *B05B 17/0638* (2013.01);
(Continued)

(58) Field of Classification Search
CPC ............ B05B 17/0607; B05B 17/0615; B05B 17/0638; B05B 17/0646
USPC ................ 239/4, 102.1, 102.2, 154, 326, 338
See application file for complete search history.

(56) References Cited

U.S. PATENT DOCUMENTS

| | | | |
|---|---|---|---|
| 4,235,378 | A | 11/1980 | Geller et al. |
| 5,456,626 | A | 10/1995 | Ming-Kang |

(Continued)

FOREIGN PATENT DOCUMENTS

| | | | |
|---|---|---|---|
| GB | 1411996 | A | 10/1975 |
| GB | 2405097 | A | 2/2005 |
| WO | 2009090909 | A1 | 7/2009 |

OTHER PUBLICATIONS

International Search Report for PCT/GB2010/002098 dated Feb. 16, 2011.
(Continued)

*Primary Examiner* — Ryan Reis
(74) *Attorney, Agent, or Firm* — Norris McLaughlin & Marcus PA

(57) ABSTRACT

Disclosed are devices which generate a mist of a treatment composition, viz, an aerosolized treatment composition which imparts a technical benefit to surfaces, or airspaces, which come into contact with the said aerosolized treatment composition. Also disclosed are methods for the treatment of surfaces utilizing the devices of the invention.

18 Claims, 18 Drawing Sheets

(51) Int. Cl.
 B08B 3/12 (2006.01)
 A61M 35/00 (2006.01)
 B05B 15/00 (2006.01)
(52) U.S. Cl.
 CPC ............ B05B 17/0661 (2013.01); B08B 3/12 (2013.01); *B05B 17/0623* (2013.01)

(56) References Cited

U.S. PATENT DOCUMENTS

| | | | |
|---|---|---|---|
| 6,273,342 B1* | 8/2001 | Terada et al. | 239/102.2 |
| 7,350,520 B1 | 4/2008 | Richard-Bey | |
| 7,628,339 B2* | 12/2009 | Ivri et al. | 239/102.2 |
| 7,677,467 B2* | 3/2010 | Fink et al. | 239/8 |
| 7,784,712 B2* | 8/2010 | Wang et al. | 239/102.2 |
| 2003/0234298 A1* | 12/2003 | Chen | 239/102.2 |
| 2004/0256487 A1* | 12/2004 | Collins et al. | 239/338 |
| 2007/0235555 A1* | 10/2007 | Helf et al. | 239/102.2 |
| 2008/0223953 A1 | 9/2008 | Tomono et al. | |
| 2009/0134235 A1* | 5/2009 | Ivri | 239/4 |
| 2009/0212133 A1* | 8/2009 | Collins, Jr. | 239/338 |
| 2009/0272818 A1* | 11/2009 | Valpey et al. | 239/102.2 |

OTHER PUBLICATIONS

International Search Report for PCT/GB2010/002097 dated Feb. 16, 2011.
International Search Report for PCT/GB2010/002099 dated Feb. 16, 2011.
Written Opinion of International Search Report for PCT/GB2010/002097 dated Feb. 16, 2011.
Written Opinion of International Search Report for PCT/GB2010/002099 dated Feb. 16, 2011.

* cited by examiner

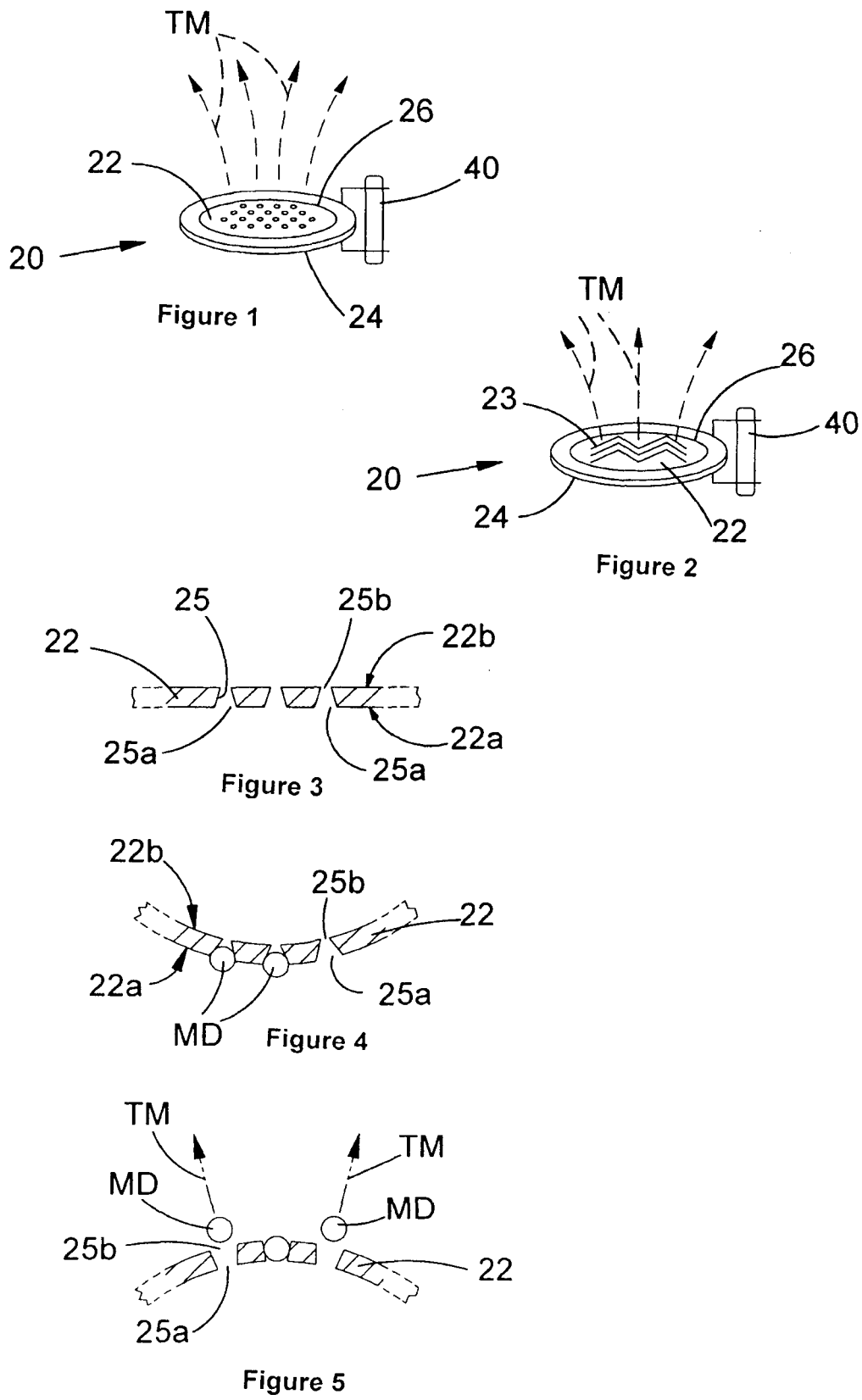

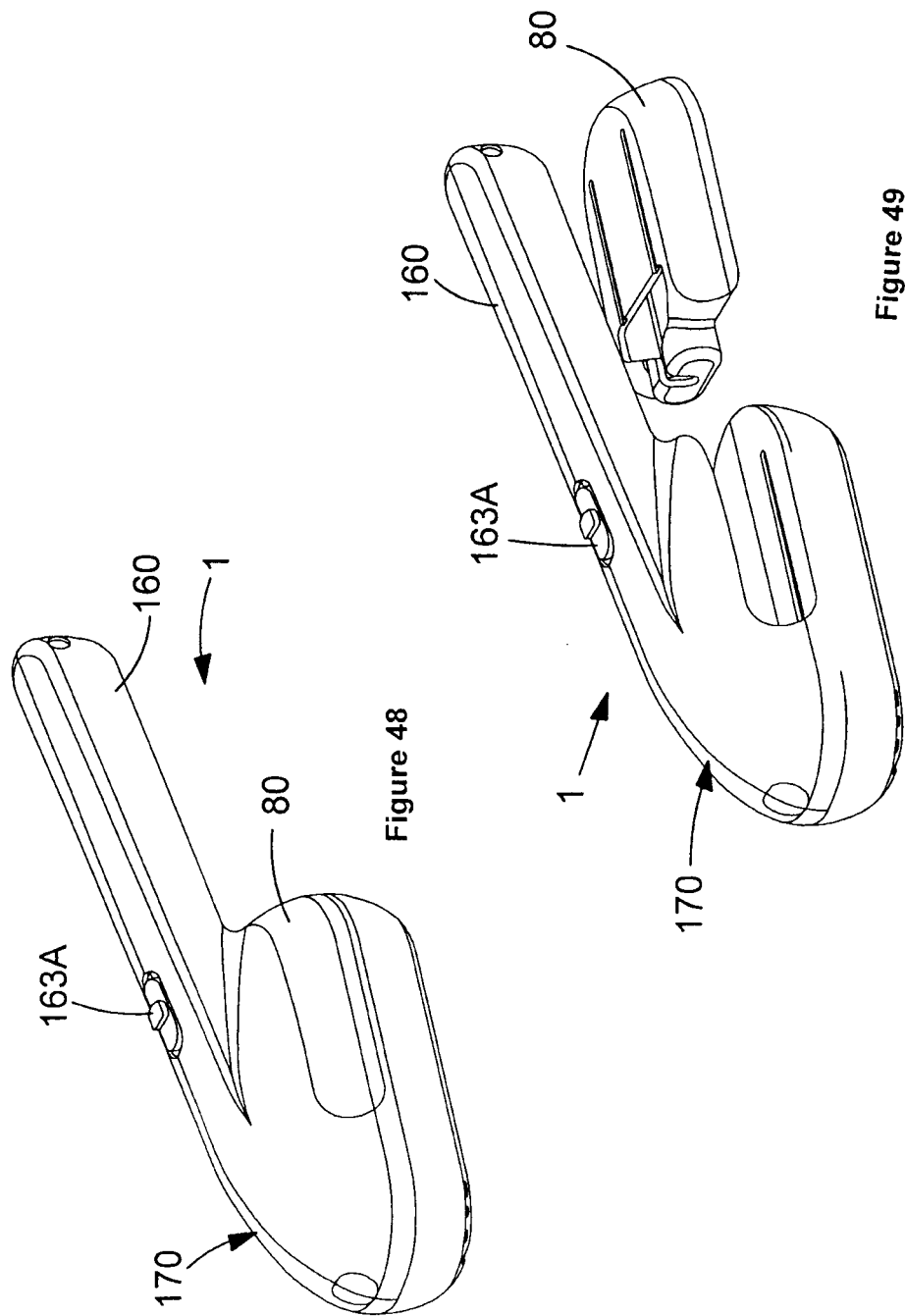

ULTRASONIC SURFACE TREATMENT DEVICE AND METHOD

This is an application filed under 35 USC 371 of PCT/GB2010/002098, filed on 16 Nov. 2010, which claims the priority benefit of U.S. Ser. No. 61/262,402 filed on 18 Nov. 2009.

The present invention relates to devices directed to devices and methods for delivering treatment compositions to a surface, e.g., an inanimate hard surface or an inanimate soft surface, and methods for treating such surfaces.

Chemical compositions for providing a technical benefit to a surface are notoriously old and known to the art. Liquid compositions, which are frequently largely aqueous in their composition, may be supplied to a surface by any of a number of means including simply pouring a quantity of such a composition of the surface or delivering it in the form of droplets which are delivered from a dispensing container. Widely used dispensing containers include pressurized container such as aerosol canisters which include a quantity of the composition as well as a propellant, as well as nonpressurized flasks or vessels which are equipped with a manually-pumpable spray head which can be used to dispense the compositions via a nozzle. While such are effective in many circumstances, they're not without disadvantages. Typically, the delivery rate using an aerosol canister or a manually-pumpable spray head is effective, but the relatively large droplets delivered by such means typically quickly saturate a hard or soft surface upon which they are dispensed. Further, the relatively large individual droplets delivered by such means are also often of a wide range of particle sizes, masses, or diameters which provide a very low degree of uniformity with regard to the distribution of the average droplet particle size being delivered. While such as advantageous where a large quantity of such treatment composition is intended to be relatively quickly delivered or deposited onto a surface, such is also disadvantageous as the relatively large droplet particle size quickly drops to the surface and provides a limited degree of distribution of the treatment composition onto a hard or soft surface. Thus, there is a real need in the art for providing improved methods for the delivery of treatment compositions to surfaces, including hard or soft surfaces. It is to such a need that the present invention is directed.

Also generally known to the technical arts primarily directed to air treatment, e.g., dispersion of fragrances, perfumes, insecticides, air fresheners, odor neutralizers, into an airspace are various devices for dispensing a liquid composition in the form of dispersed particles. Such include those disclosed in U.S. Pat. No. 7,694,892 to Feriani, et al.; US 2009/308945 to Tollens, et al.; US 2009/272818 to Valpey III, et al.; U.S. Pat. No. 5,299,739 to Takahashi et al.; which disclose various devices which include a vibrating plate and a wick or capillary for delivery of liquids from a reservoir to the vibrating plate. Further, US 2004/0256487 to Collins, Jr. et al., and US 2005/0103891 to Abergel, et al. and U.S. Pat. No. 6,802,460 to Hess, et al. disclose spraying devices which include a vibrating plate in direct fluid contact with liquid from a reservoir. U.S. Pat. No. 5,297,734 discloses various arrangement of vibrating plates supplied with liquids for delivering particulates of the liquid to an airspace. The contents of these US patent documents are herein incorporated by reference.

Notwithstanding these known art devices, further advances are still needed in the art treatment devices and treatment methods.

FIG. 1 depicts an embodiment of a mist generator means.

FIG. 2 depicts an alternative embodiment of a mist generator means.

FIG. 3 depicts a portion of a vibrating plate of a mist generator means.

FIG. 4 depicts a portion of a vibrating plate of a mist generator means.

FIG. 5 depicts a portion of a vibrating plate of a mist generator means.

Figure 18:
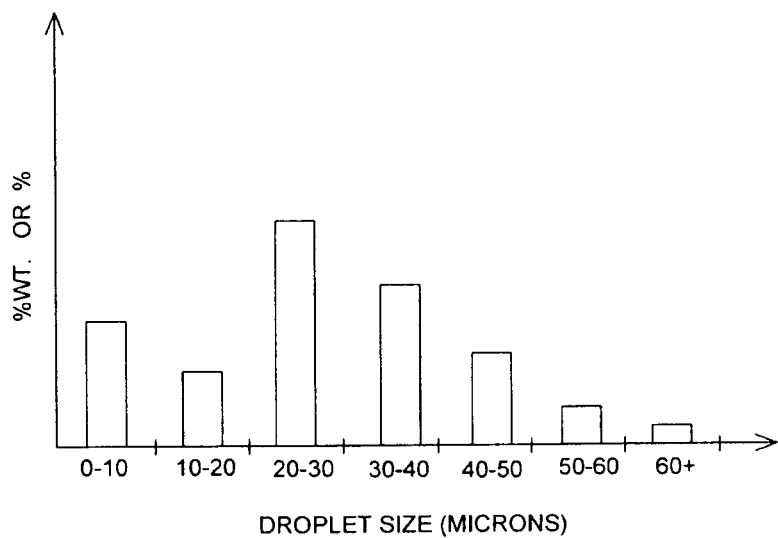

FIG. 18 provides a graph illustrating a mass distribution or a % distribution of the size (in microns) of the discrete liquid droplets being dispensed by a mist generator means.

Figure 19:
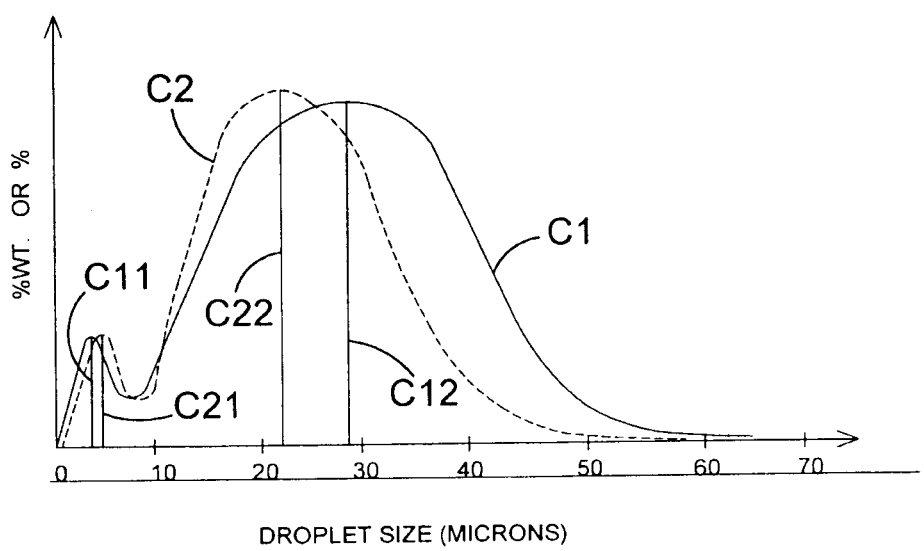

FIG. 19 provides a graph illustrating two further alternative bi-modal distributions of discrete liquid droplets or particles of the treatment composition present in a treatment mist formed from a mist generator means.

Figure 20:
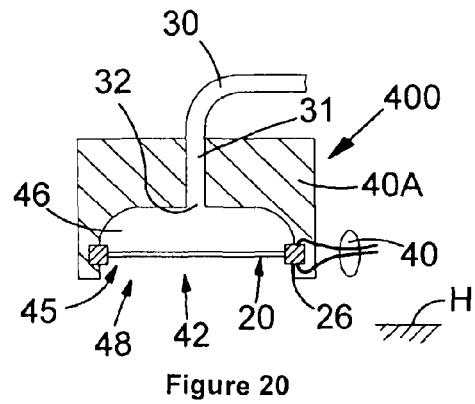

FIG. 20 illustrates an embodiment of a mist generator means.

Figure 21:
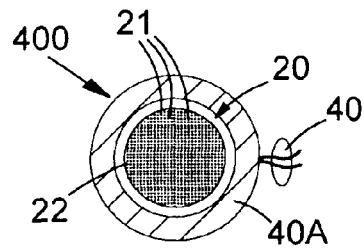

FIG. 21 illustrates a further view of the embodiment of a mist generator means of FIG. 20.

Figure 22:
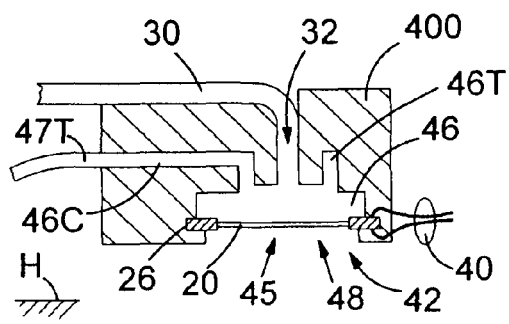

FIG. 22 depicts in a cross-sectional view an embodiment of a mist generator means.

Figure 23:
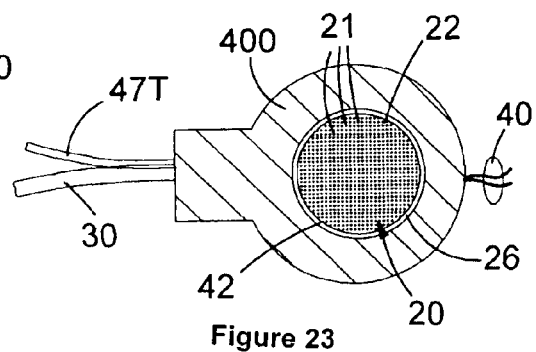

FIG. 23 depicts in a further view of the embodiment of the mist generator means of FIG. 22.

Figure 24:
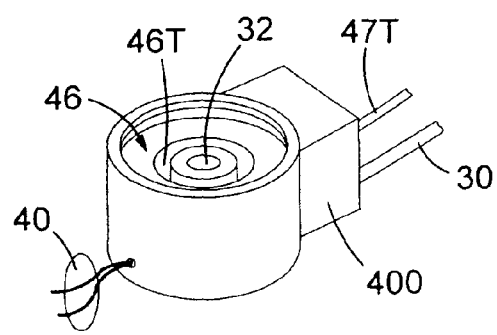

FIG. 24 depicts in a further view of the embodiment of the mist generator means of FIG. 22.

Figure 25:
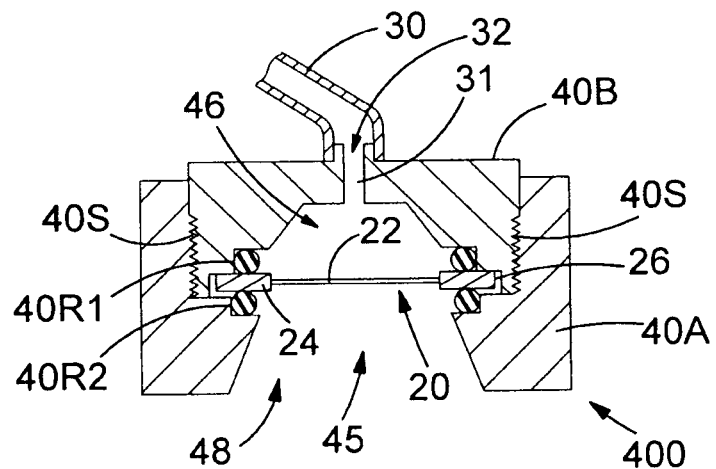

FIG. 25 provides a cross-sectional view of an embodiment of a mist generator means.

Figure 26:
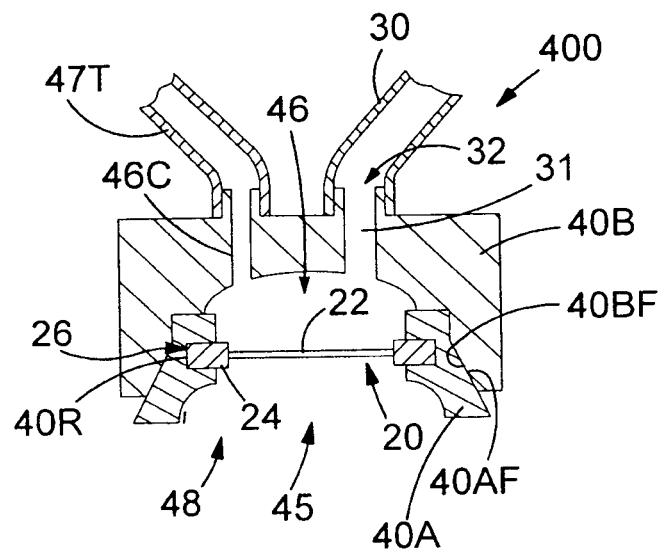

FIG. 26 provides a cross-sectional view of an embodiment of a mist generator means.

Figure 27:
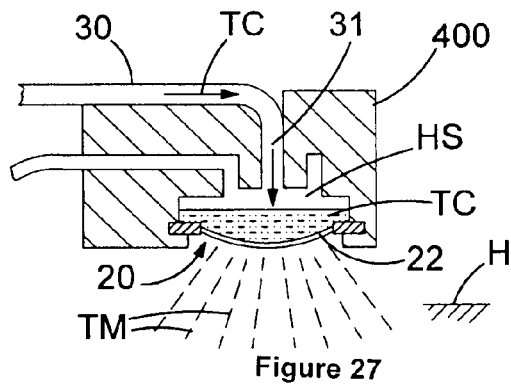

FIG. 27 provides a view of a mist generator assembly generally in accordance with the embodiment of FIG. 22 in a first mode of operation.

Figure 28:
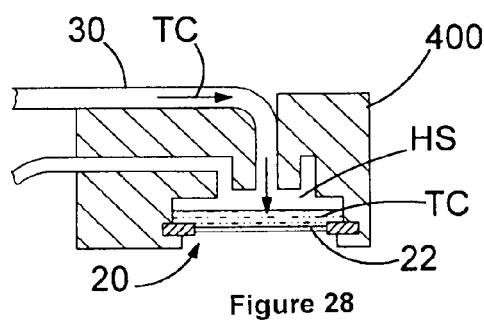

FIG. 28 provides a view of a mist generator assembly generally in accordance with the embodiment of FIG. 22 in a second mode of operation.

Figure 29:
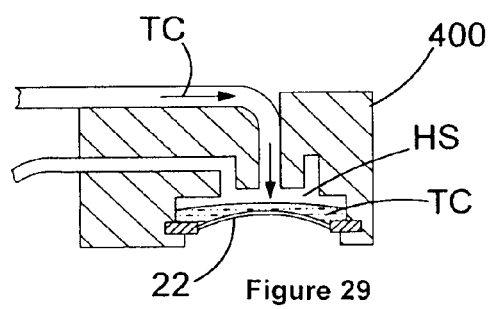

FIG. 29 provides a view of a mist generator assembly generally in accordance with the embodiment of FIG. 22 in a third mode of operation.

Figure 30:
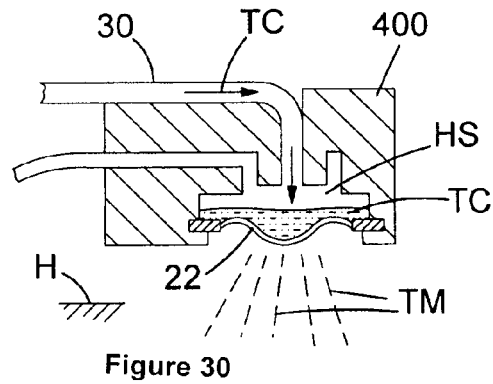

FIG. 30 depicts a view of a mist generator assembly generally in accordance with the embodiment of FIG. 22 in first state of operation.

Figure 31:
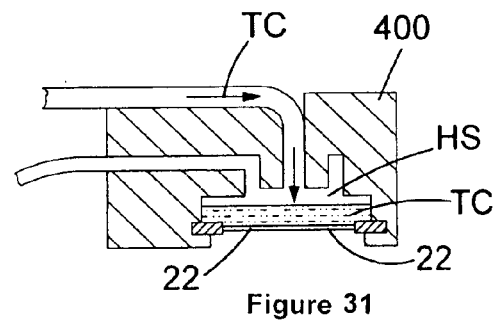

FIG. 31 depicts a view of a mist generator assembly generally in accordance with the embodiment of FIG. 22 in a further state of operation.

Figure 32:
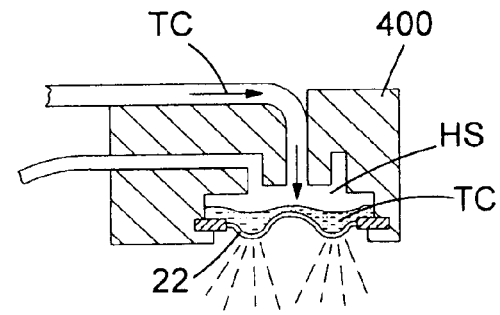

FIG. 32 depicts an additional view of a mist generator assembly generally in accordance with the embodiment of FIG. 22 in a still further state of operation.

Figure 33:
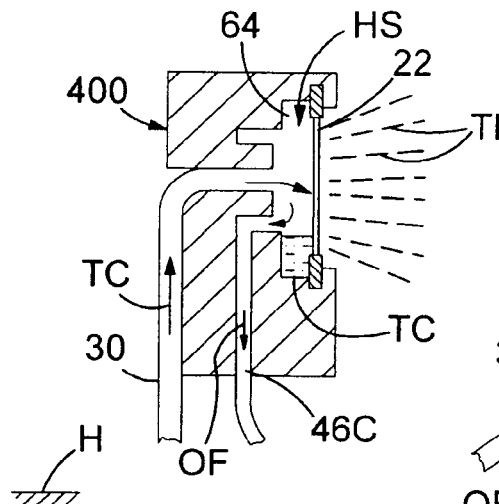

FIG. 33 depicts a view of the mist generator assembly of FIG. 22 in a first orientation.

Figure 34:
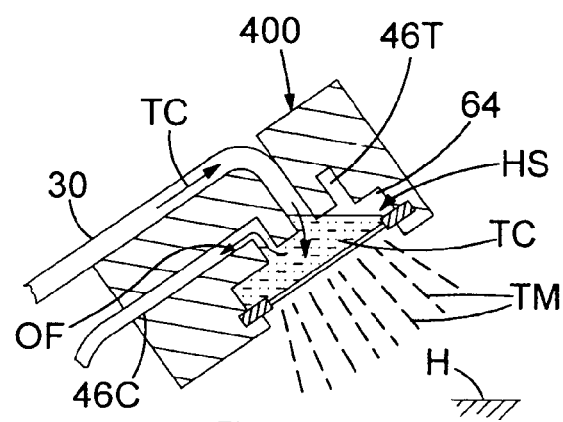

FIG. 34 depicts a view of the mist generator assembly of FIG. 22 in a second orientation.

Figure 35:
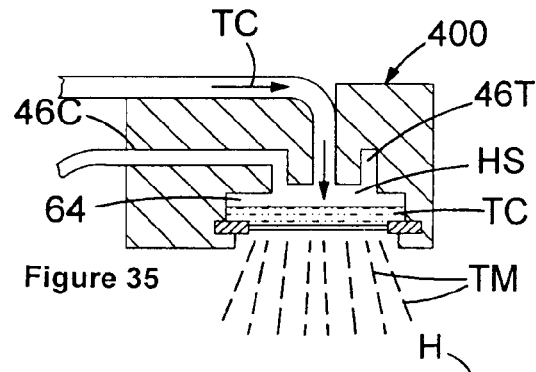

FIG. 35 depicts a view of the mist generator assembly of FIG. 22 in a third orientation.

Figure 36:
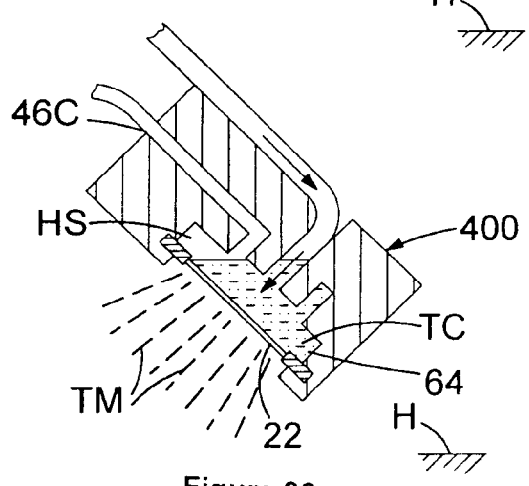

FIG. 36 depicts a view of the mist generator assembly of FIG. 22 in a fourth orientation.

Figure 37:
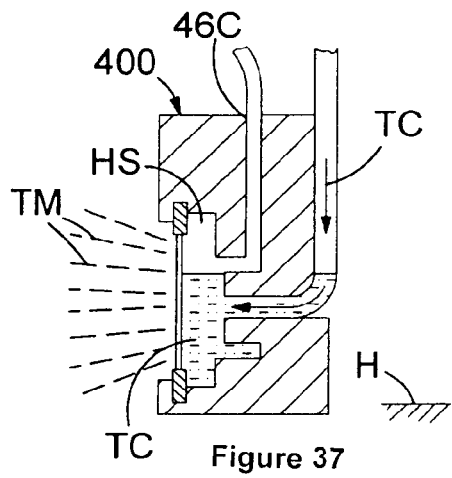

FIG. 37 depicts a view of the mist generator assembly of FIG. 22 in a fifth orientation.

Figure 38:
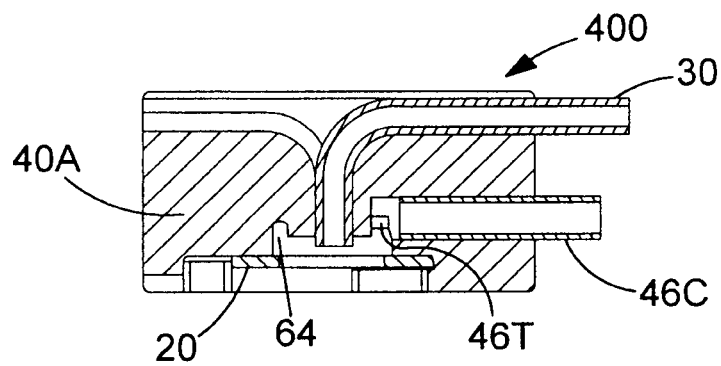

FIG. 38 illustrates a view of a preferred embodiment of a mist generator assembly of the invention.

Figure 39:
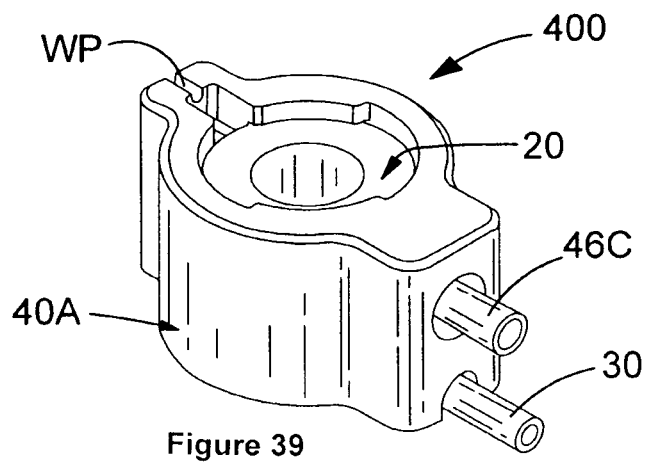

FIG. 39 illustrates a further view of a preferred embodiment of a mist generator assembly of the invention.

Figure 40:
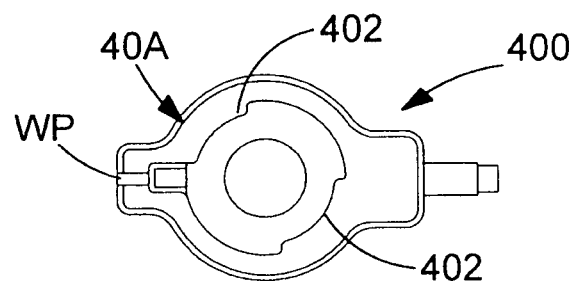

FIG. 40 illustrates a further view of a preferred embodiment of a mist generator assembly of the invention.

Figure 41:
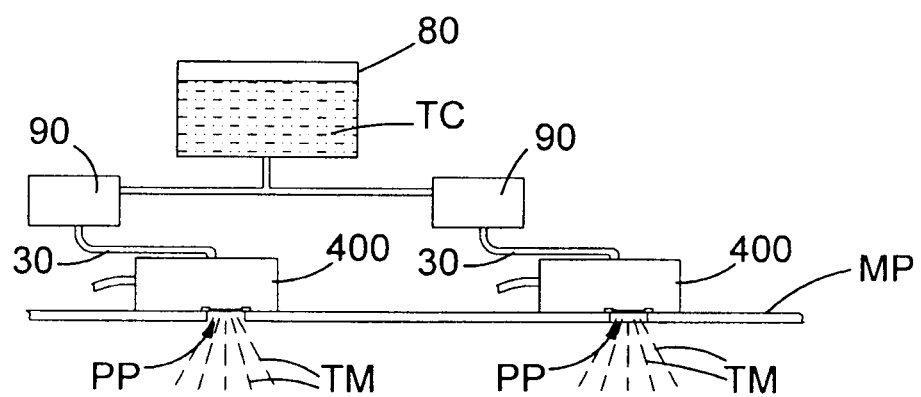

FIG. 41 illustrates a representational view of a pair of mist generator assemblies.

Figure 42:
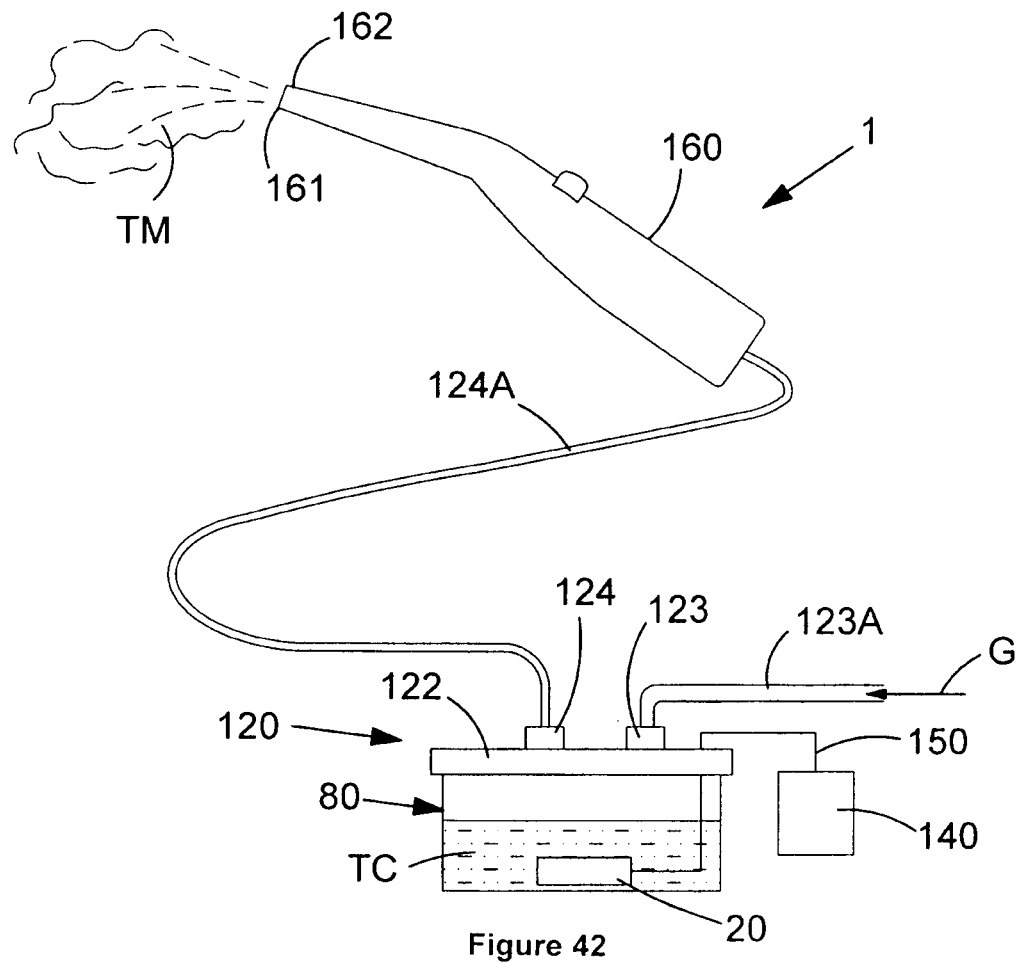

FIG. 42 depicts an one embodiment of a device according to the present invention which includes a grippable control handle which can be used to deliver a quantity of the mist of the treatment composition to a desired location.

Figure 43:
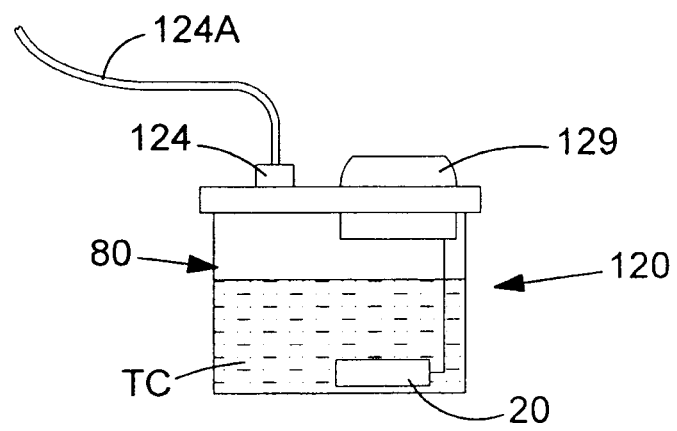

FIG. 43 illustrates a self-contained embodiment of a first assembly of a device of the invention.

Figure 44:
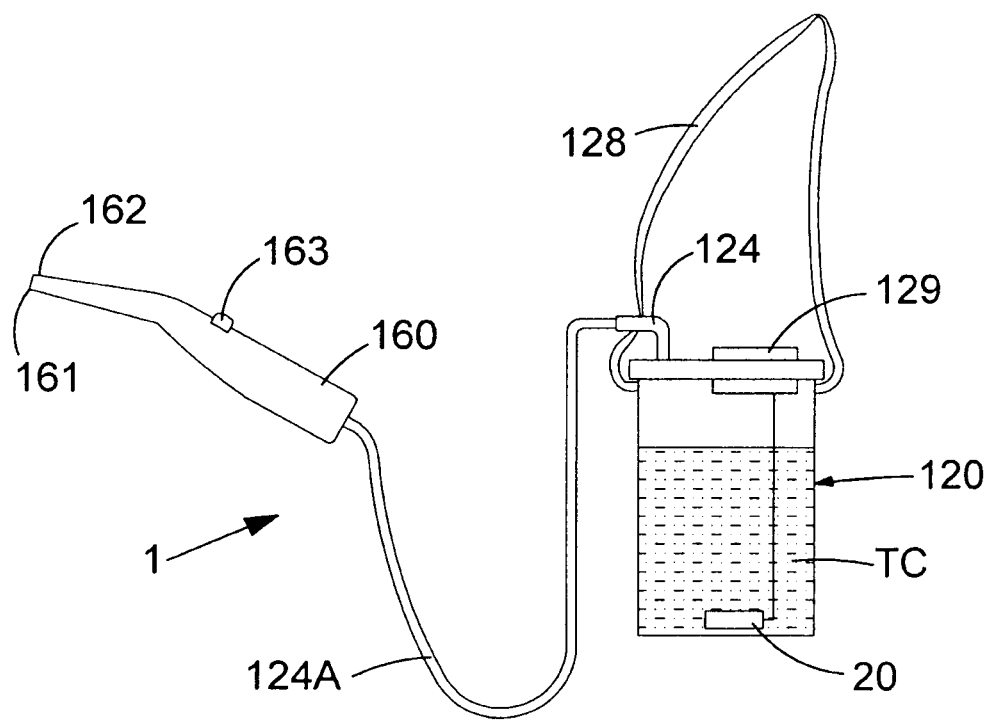

FIG. 44 depicts a device according to the invention which includes the first assembly attached to a flexible strap which can be used to hang the first assembly 120 from a body part such as a shoulder.

Figure 45:
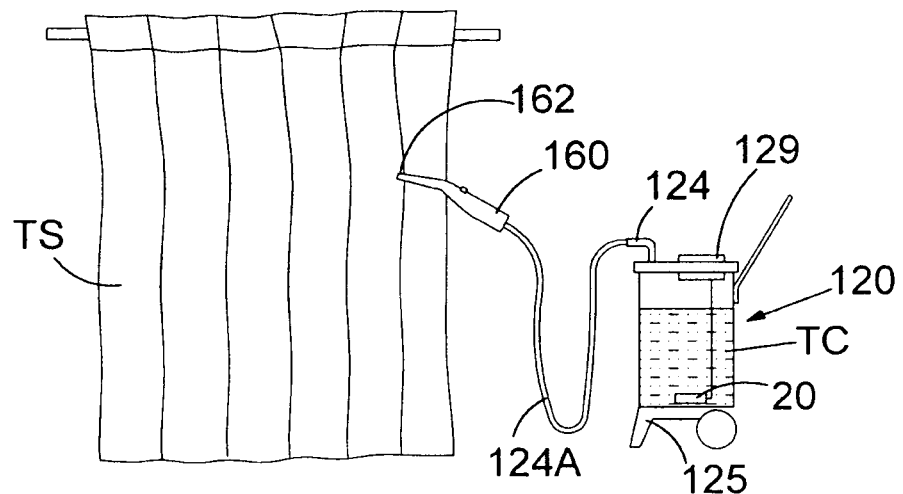

FIG. 45 depicts a further embodiment of a device wherein a first assembly is provided on a wheeled cart, such as may be desired when a large amount of the treatment composition in the form of the mist is required to be dispensed.

Figure 46:
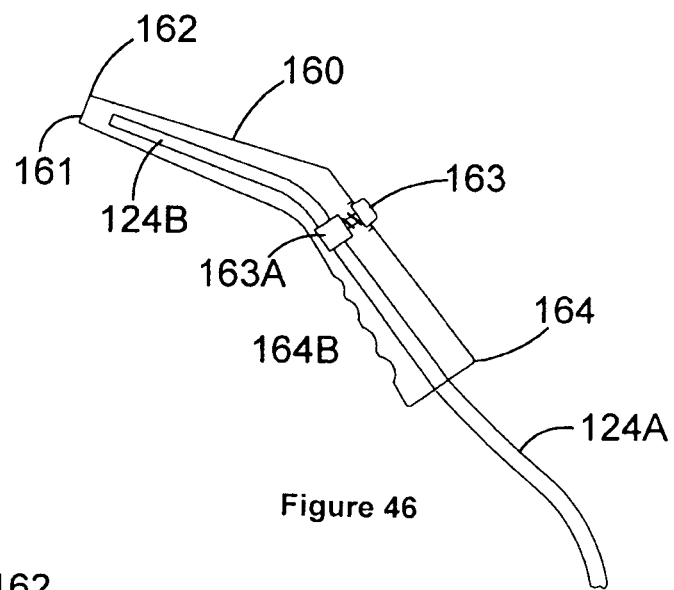

FIG. 46 illustrates a cross-sectional view of an embodiment of a device in a self-contained and portable assembly.

Figure 47:
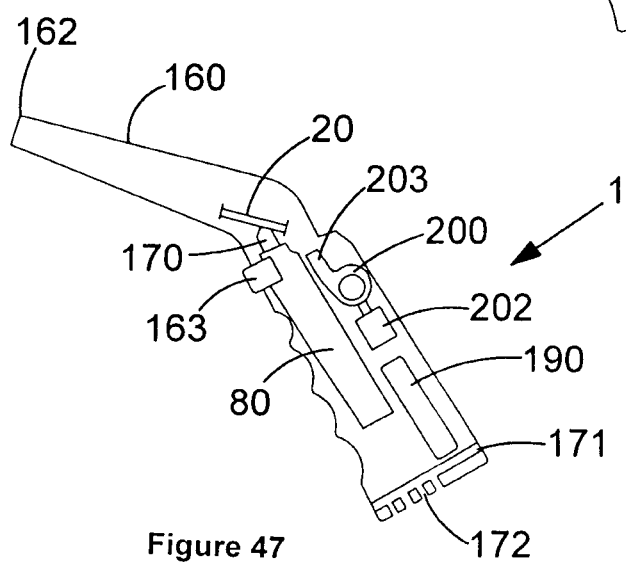

FIG. 47 illustrates a cross-sectional view of a further embodiment of a device in a self-contained and portable assembly.

FIG. 48 illustrates a view of a portable embodiment of the invention.

FIG. 49 illustrates a view of a portable embodiment of the invention.

Figure 50:
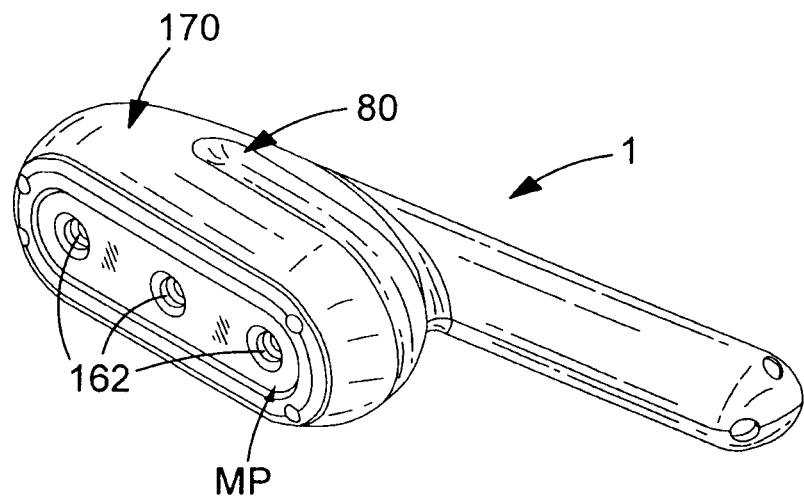

FIG. 50 illustrates a view of a portable embodiment of the invention.

Figure 51:
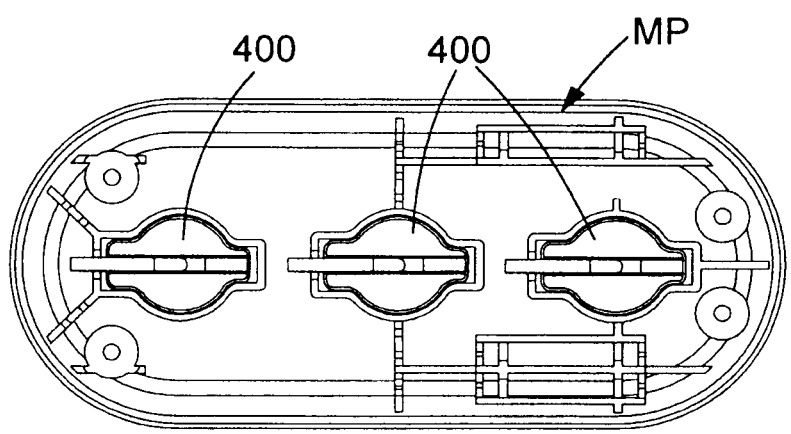

FIG. 51 illustrates a view of a portable embodiment of the invention.

Figure 52:
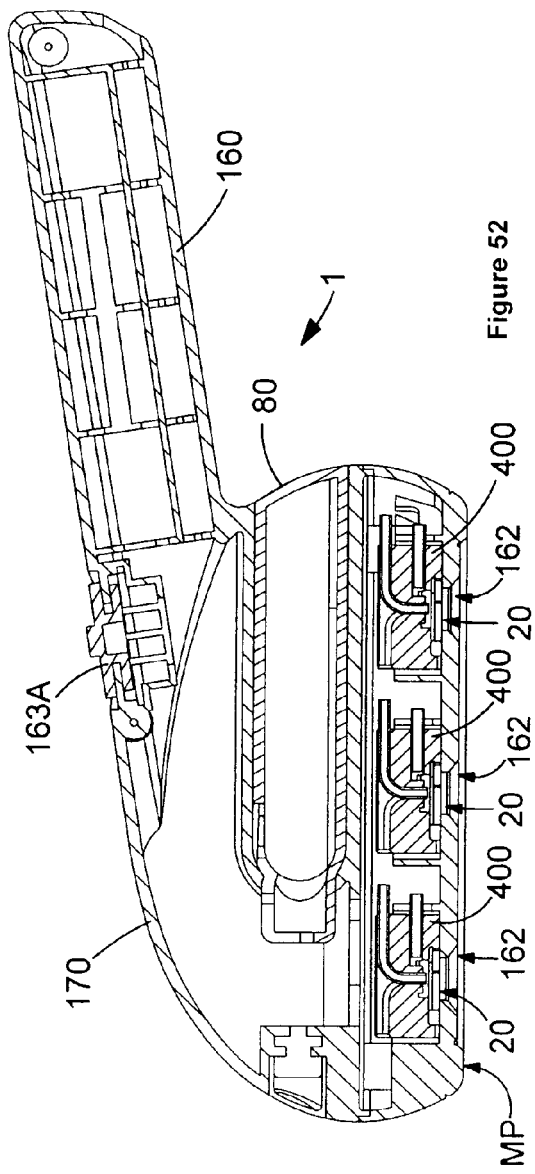

FIG. 52 illustrates a view of a portable embodiment of the invention.

Figure 53:
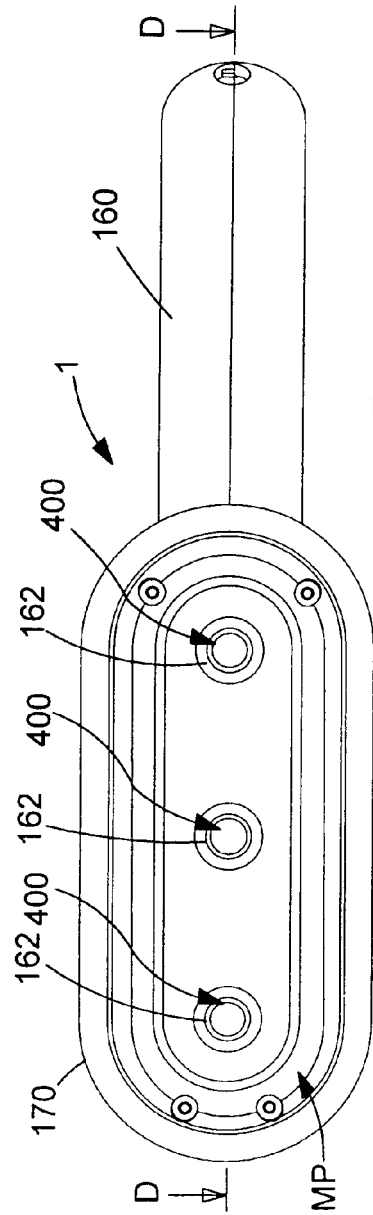

FIG. 53 illustrates a view of a portable embodiment of the invention.

Figure 54:
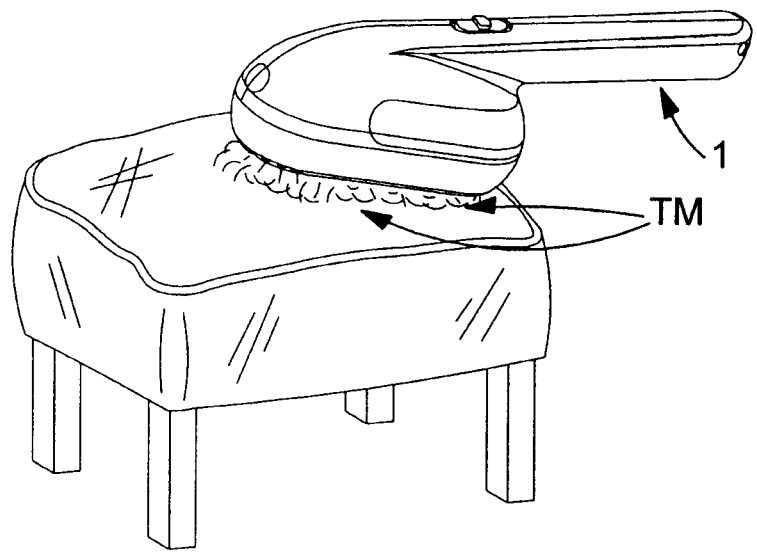

FIG. 54 depicts a simplified manner of treating a textile surface utilizing a device according to an aspect of the invention.

Figure 55:
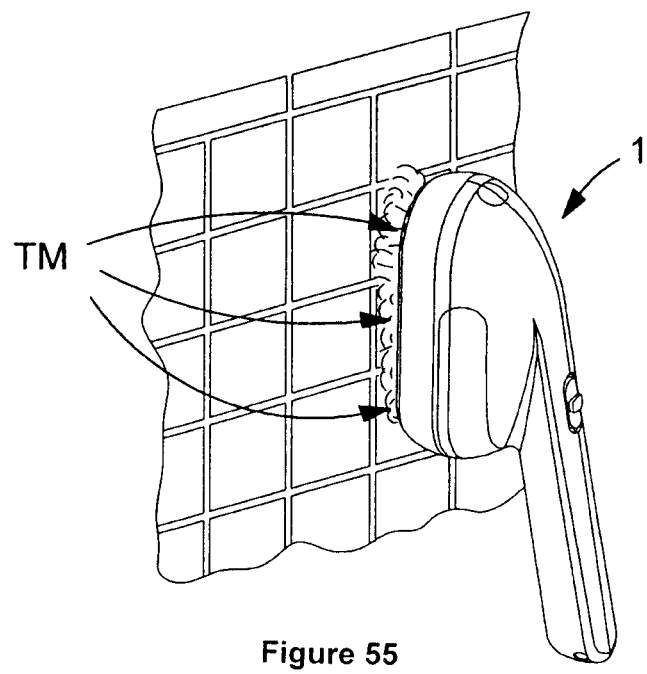

FIG. 55 depicts a simplified manner of treating a hard surface using a device according to an aspect of the invention.

In one aspect of the present invention provides a device which generates a mist of a treatment composition, viz, an aerosolized treatment composition which imparts a technical benefit to surfaces, or airspaces, which come into contact with the said aerosolized treatment composition.

According to a further aspect of the invention, there is provided a method for the treatment of hard surfaces and soft surfaces which method comprises the step of providing a device which generates a mist of a treatment composition, which treatment composition contacts the surface and provides a technical benefit thereto.

According to an additional aspect of the invention, there is provided a method for the treatment of inanimate, nonporous hard surfaces which method comprises the step of providing a device which generates a mist of a treatment composition, which contacts hard surfaces and provides a technical benefit thereto.

According to a further aspect of the invention, there is provided a method for the treatment of soft surfaces. e.g., carpets, rugs, upholstery, curtains and drapes, fabrics, textiles, garments, and the like which method comprises the step of providing a device which generates a mist of a treatment composition, which treatment composition contacts the soft surfaces and which optionally further also penetrates the surface or surfaces thereof, and which provides a technical benefit thereto.

According to a yet further aspect of the invention, there is provided a method for controlling the incidence of dust mites, or controlling their residual fecal matter which method comprises the step of providing a device which generates a mist of a treatment composition, which treatment composition contacts the surface and provides a technical benefit thereto.

In a further aspect of the invention there is provided a method for denaturing allergens, which method comprises the step of providing a device generates a mist of a treatment composition, which treatment composition contacts the surface and provides a technical benefit thereto.

In a yet further aspect of the invention there is provided a method for the pre-treatment of an article, or the post-treatment of an article treated in a laundry machine for the laundering treatment of fabrics, textiles, garments, and the like which method comprises the step of providing a device which generates a mist of a pre-treatment composition, which mist contacts the aforementioned fabrics, textiles, garments, and the like and which optionally further also penetrates the surface or services thereof, and which provides a technical benefit thereto. Such pre-treatment step or post-treatment step may be practiced directly to said article, or may be practiced utilizing a machine such as a laundry washing machine or a laundry drying machine.

According to a further aspect of the invention there is provided a method for the pre-treatment of an article, or the post-treatment of an article such as a dishware article, treated in an automatic dishwashing machine, which method comprises the step of providing a device which generates a mist of a pre-treatment composition, which said composition contacts dishware e.g., tableware, glassware, cooking utensils, cookware, and the like, and which provides a technical benefit thereto. Such pre-treatment step or post-treatment step may be practiced directly to said dishware article, or may be practiced utilizing a machine such as an automatic dishwashing machine.

In a still further aspect of the invention there is provided a method for the delivery of an air treatment composition to an airspace, which method comprises the step of providing a device which generates a mist of a treatment composition, which treatment composition contacts said airspace and provides a technical benefit thereto, e.g., fragrancing, perfuming, odor masking, malodour neutralization, air sanitization, and the like. The method may be practiced within an open airspace, e.g., a larger volume such as a room, public space within the interior of a building, a cabin or compartment within a vehicle, as well as within a closed container or other relatively smaller space, e.g., the interior of a storage cabinet, a closet, a shower stall, a garbage container or refuse bin, and the like.

According to a still further aspect of the invention, there is provided a method for the application of a treatment composition to a bodily surface, e.g., a dermal surface, or hair surface, e.g., a skin surface with hair growth thereon, which method comprises the step of providing a device which generates a mist of a treatment composition which composition contacts the bodily surface and provides a technical benefit thereto.

These and further aspect of the invention will be more apparent from a review of the following specification and accompanying drawings.

In one aspect of the present invention provides a device which generates a mist of a treatment composition, also referred to as an aerosolized treatment composition which imparts a technical benefit to surfaces, or airspaces, which come into contact with the said aerosolized treatment composition. According to one embodiment, there is provided a device for aerosolizing a fluid product, which device includes a mist generator, a control circuit for operating the mist generator, a reservoir for the fluid product to be aerosolized, a means for supplying the a mist generator with the fluid product, a housing, and optionally at least one flow directing nozzle or flow directing orifice adapted to direct the flow of a mist generated by the mist generator out from the device.

In a second aspect of the invention the device is divided into two or more parts, which may be interconnected to function to provide a mist of the treatment composition.

In a third aspect of the invention the device is fully hand holdable and generates a mist of a treatment composition which may be used to treat a surface and/or an airspace.

The device includes a mist generator means which comprises a vibrating member which includes a metal or ceramic plate; the plate may be solid or porous, may contain passages or holes passing therethrough, be micropierced with perforations in the form of a grid or in the form of one or more segments or slots passing through the vibrating member, and a piezoelectric actuator which, when operated, causes vibratory motion in the vibrating member. The mist generator means may be an annular ring of a piezoelectric material which is attached to said vibrating member and spans the annulus, which when activated, causes the said vibrating member to vibrate. The mist generator means may comprise a piezoelectric material which is attached to, adjacent to or abutting a non-vibrating element or member which receives the vibratory motion of the piezoelectric material and transfers the vibratory motion to the said vibrating member. The mist generator means may comprise a piezoelectric material which is attached to, adjacent to or abutting a non-vibrating element or member which receives the vibratory motion of the piezoelectric material and forces the treatment composition through the vibrating member which optionally but not necessarily vibrates; where the mesh or plate does not vibrate the treatment composition is driven through the vibratory member by virtue of the movement of the attached to, adjacent to or abutting a non-vibrating element or member which receives the vibratory motion of the piezoelectric material, e.g. by compression of the treatment composition located between the non-vibrating member and the mesh or plate due to the vibratory motion of the piezoelectric material.

The mist generator means may be a tubular piezoelectric material which includes a vibrating member spanning its interior bore between the ends of the piezoelectric material, and/or includes a vibrating member spanning the interior bore at one or more ends thereof, such that when activated the tubular piezoelectric material vibrates or expands/contracts which in turn imparts vibratory motion of the vibrating member(s).

The mist generator means may form a part of the device and be permanently affixed thereto. The mist generator means may form part of a further element or part of the device, such as a mist generator assembly as described hereafter. Alternately the mist generator means may be provided as part of a refill unit or refill reservoir which, when inserted or affixed to the device completes the device and enables its use. Further the mist generator means may be user replaceable article or unit which may be removed and/or installed as needed or desired by a user to one or more of the device or the refill unit or refill reservoir. Yet further, in any embodiment, the mist generator may be formed of several parts which are required to be assembled in order to form an operating mist generator means, e.g., a piezoelectric actuator may form part of the device and a separate vibrating member form part of a refill unit or refill reservoir which remains inoperative until the device and refill unit or refill reservoir are properly aligned or otherwise installed in the device so permit the interaction between the piezoelectric actuator and the vibrating member which then operates as a mist generator means. Such an embodiment is preferred in that with the replacement of a refill unit or refill reservoir a new vibrating member is provided to the device.

The device includes a controller means for controlling the operation of the mist generator means. The controller means may provide one or more functions. The controller means preferably includes a high frequency generator used to generate a suitable electrical signal for the operation of the mist generator, and particularly a piezoelectric element or device associated therewith. The controller means may include one or more switches, or other input means, e.g., buttons, contacts or switches, which can be established by user of a device according to the invention in order to control the mode of operation of the controller means. The controller means may also include means for controlling the output of the mist generator which may turn the unit off, or suspend its operation after a metered amount or dose of the treatment composition is dispensed from the device; the amount of the treatment composition may be a user controllable amount. e.g., via a setting, or may be a predetermined metered amount which cannot be changed by the user. The amount of treatment composition delivered by the device may be varied in response to a signal received by the controller means which may respond to an environmental condition of the device. The controller means may also be adapted to receive, and respond to, one or more signal inputs received from one or more sensors associated with the device. For example the controller means may be adapted to receive and respond to signals or conditions relating to the status of any part of the device such as the quantity of treatment composition in a reservoir or refill unit, to the physical orientation of the device, as well as to the frequency of dispensing and/or volume of treatment composition dispensed over a unit time interval. Nonlimiting examples of such responses include to increase or decrease one more of: the volumetric delivery rate of the treatment composition, and/or the frequency of delivery of the treatment composition per unit of time. The controller means may provide one or more output signals which may be transmitted to one or more further elements of the device via suitable conductor means, such as wires, in order to control their operation. The controller means may be programmable and include suitable electronic circuitry for the operation of the device according to one or more programs each having at least one, but preferably a plurality of, discrete programmed steps; typically such includes at least a logic or program controller, e.g., a central processing unit, and system memory for storing one or more programs. The controller means may be a non-programmable circuit, which preferably operates according to specific logic responsive to one or more signal inputs to the controller means. The controller means may comprise a drive circuit in order to provide suitable power and/or signal outputs to the mist generator in order to control its operation in generating a treatment mist from the fluid treatment composition, which may include known-art drive circuits suitable for this purpose. One example of a suitable circuit which may be present within the controller means is a pulse-width-modulation circuit comprising a transformer converter and having an input acted on by a piezoelectric element present and the mist generator; such as disclosed in published application US 2009/0121043, the contents of which is herein incorporated by reference. A further example of a suitable circuit is one which includes a microprocessor controlled variable oscillator for providing variable frequencies to mist generator such that treatment composition is formed into an aerosol of fine droplets. The variable oscillator preferably comprises a digital resistor for adjusting the time of charge and discharge; such a circuit is disclosed in U.S. Pat. No. 7,673,812, the contents of which are incorporated by reference. The device may be operated by direct control by a user. e.g., controlling a switch upon the device or alternately, the device may be operated indirectly. e.g., by a remote control unit.

The device may include a power supply source which is integral to the device. e.g., one or more batteries, such that the device is portable, or the device may include means, e.g. wire, for connecting the device to a source of power, e.g., a transformer or electrical mains, supplying electrical power to the controller means. The batteries may be replaceable by the user when they are exhausted. The batteries may be rechargeable batteries which may be replenished by connecting them to a suitable power source. Thus in certain embodiments the device of the invention is fully portable, but in other embodiments the device of the invention or part thereof may be a stationary part which is not necessarily moved or portable when the device is in use. Such includes, e.g., a recharging station, or a part of the device which comprises the fluid reservoir. Further configurations of the device are also possible.

The device may include one or more sensor means. Sensor means may be present to evaluate the state of a condition within the device, e.g., the presence of a treatment composition, or the presence of a suitable refill container. Sensor means may be present to evaluate the state of the environment in which the device is being used, e.g., time of day, degree of brightness near the environment of the device, absence of light, presence of light, a sound sensor, a vibration sensor, a heat sensor, an odor or scent sensor, a pressure sensor, a proximity sensor, and the like.

The device may include a fill level sensor which controls the operation of the device responsive to the amount of liquid present in the device and/or in the reservoir, which may be a removable reservoir.

The device may include one or more orientation sensing means for determining a physical orientation of the device, which for example, can be a level sensor, horizon sensor, accelerometer or any other device which can be used to establish the relative position of the device with respect to the horizontal or horizon.

The device may include a reservoir for containing a quantity of the treatment composition, which reservoir may be a integrally formed as part of, or as an element of the device, which is not intended to be removed but rather refilled with the treatment composition when required. Alternately the device may include a removable reservoir which is intended to be removed from the device and replaced when necessary, such as to replenish or to resupply a new quantity of the treatment composition to the device. The reservoir of the device may be adapted to contain a single fluid treatment composition or may be adapted to contain a plurality of fluid treatment compositions. Such a removable reservoir may take the form of cartridge or assembly, or be a part of such a cartridge or assembly. The cartridge may be a single-use cartridge which is not intended to be refilled. The cartridge may include a bag or plenum which may optionally be vented to the atmosphere. The cartridge may be refillable by the user.

The device may include at least one fluid control means for controlling the rate of delivery of a fluid product, viz., a treatment composition, from the reservoir to the mist generator. The fluid control means may form part of the device, or may be part of a removable reservoir, or may be present in both the device and a removable reservoir. The fluid control means may also be formed by cooperative elements, part of which are present on the removable reservoir and part on the device such that, when the cooperative elements are assembled, in conjunction they form a fluid control means. The device may include one, or several fluid control means. Nonlimiting examples of fluid control means include the following: a) one or more tubes or channels which provide fluid conduits to supply the treatment composition from the fluid reservoir to the mist generator means; b) one or more pumps, especially preferably one or more micropumps, c) direct physical interaction between a vibrating member and the treatment composition, e.g. wherein the treatment composition is supplied to a top surface or bottom surface of the vibrating member during at least a portion of its range of vibratory (or oscillatory) movement, or during the range of vibratory (or oscillatory) movement the vibrating member contacts a quantity of the treatment composition and entrains it within the vibrating member before expelling it therefrom, such for example may occur wherein a tube having exposed treatment composition at an end thereof is in near proximity but not in direct contact with a vibrating member; d) by a gravity feed flow of the treatment composition to the mist generator means; e) a manual supply means, e.g., manual pumping by a user of an element such as a pump or bulb which transfers a quantity of the treatment liquid to the mist generator means; f) an antechamber or cavity which is intermediate the reservoir and the mist generator means which antechamber or cavity is first filled from the reservoir, and the mist generator means is supplied with treatment composition from the antechamber of cavity which had been previously supplied treatment composition from the reservoir. An antechamber may form part of a further element or component which also includes the mist generator means, e.g., may form part of a mist generator assembly.

Particularly preferred fluid flow means include b) one or more pumps, including but not limited to: gear pumps, positive displacement pumps, rotary pumps, micropumps, diaphragm pumps, and especially preferably piezoelectric diaphragm pumps such as those presently commercially available from Bartels Mikrotechnik GmbH (Dortmund, Germany). Examples of such piezoelectric diaphragm pumps are disclosed in one or more of the following: WO/2009/059664, the contents of which are herein incorporated by reference. Such number among particularly preferred embodiments of the invention.

The device may include at least one fluid control means for controlling the rate of delivery of a fluid product (treatment composition) from the reservoir to the mist generator. The fluid control means may form part of the device, or may be part of a removable reservoir, or may be present in both the device and a removable reservoir. The fluid control means may also be formed by cooperative elements, part of which are present on the removable reservoir and part on the device such that, when the cooperative elements are assembled, in conjunction they form a fluid control means. The device may include one, or several fluid control means.

The device may include an airflow generator means to increase the flowrate of the mist of the treatment composition.

When present, the airflow generator means may be used to generate a current of air which induces or directs the flow of the atomized treatment composition, and especially as it exits the device. The airflow generator means also entrains the nebulized or mist of the treatment composition and may be used to direct its flow outwardly from the device. However in particularly preferred embodiments such airflow generator means are absent and excluded form the device.

The device may be a single unit which is substantially confined by a housing, or the device may include one or more extensible elements, e.g., a wand connected to the housing of the device which housing contains the mist generator and/or the reservoir. In one embodiment a part of the device contains the reservoir of the treatment composition and the mist generator means, which is connected by a tube through which the atomized treatment composition (mist of the treatment composition) passes to a further part of the device which may include a flow directing nozzle through which the atomized treatment composition exits the device; the user may position the device, and when present, the flow directing nozzle, in order to direct the flow of the atomized treatment composition onto a hard surface and/or onto a soft surface in order to treat the said surface. A flow directing nozzle is not required of all embodiments of the invention and may be excluded from the device, but may be present in certain preferred embodiments of the invention.

The device may comprise further flow directing elements which cooperative with the flow directing nozzle in order to provide an ancillary flow directing benefit, or which provide means for interactively contacting the surfaces being treated. However in certain embodiments such further flow directing elements are absent and excluded form the device.

The device may further comprise an air-treatment means which is used to provide a volatile material to the ambient environment of the device, which volatile material is supplied to the ambient environment independently of the mist generator means. The air-treatment means may be used to deliver a volatile material, e.g., one or more of fragrances, perfumes, compositions for the control or eradication of airborne insects, odor neutralizing agents, odor masking agents, as well as those which may impart holistic or aromatherapy benefits which is separate from the treatment composition. For example, such a volatile material may be provided in a reservoir comprising a quantity of said volatile material which may form part of or be used with the device. Such a reservoir can take any shape or suitable form, and can be included within the interior of the device, or on the exterior of the device, or may be even be separate from the device but provided as a separate article or element which is separate or separable from the device but intended to be placed in the near proximity of the device. By way of nonlimiting examples, such a reservoir may include a porous material such as a pad or tablet which is impregnated with, or upon which is absorbed a volatile composition useful in providing an air treatment benefit, a gel or a solid composition which also contains a volatile air treatment composition which may emanate to the ambient environment from the reservoir, or a container which includes a fibrous wick, or pad, or a porous membrane for the delivery of a volatile material to the ambient environment from the reservoir. Alternately the reservoir may contain a quantity of a particulate material in the form of a single body, e.g. plate, or as a plurality of spheres, or beads which function as a reservoir for the volatile composition, and from whence they may be delivered to the ambient environment. Non-limiting examples of such materials include those currently marketed under the tradename Auracell® (ex. Rotuba Extruders) which are based on fragranced cellulosic polymers, as well as PolyIFF® (ex. International Flavors and Fragrances Inc.), as well as Tenite® (ex. Eastman Chemical Co.).

The device of the invention includes a mist generator means for the delivery of a treatment composition which comprises a treatment agent. In certain embodiments the treatment composition may be solely comprised of the treatment agent. The mist generator may be any device which provides for atomization of the treatment composition or which provides for the aerosolization of the treatment composition without directly heating the treatment composition or utilizing a propellant gas or via the use of a liquid pump to directly drive the treatment composition through a nozzle and consequently cause the formation of discrete particles therefrom.

The treatment composition may be provided in a ready to use form, e.g., does not require further dilution with water or other material in order to form the treatment composition to be atomized and dispensed from the device, or alternately may be provided in a concentrated form which requires further dilution with water or other material prior to its being atomized and dispensed from the device.

In preferred embodiments the mist generator means is a nebulizer means, which is also generally preferred for use. Nebulizer means typically impart energy to the treatment composition wherein the ultrasonic energy is supplied via a transducer. This energy results in atomization of the treatment composition without requiring direct heating of the treatment composition or without the need for a propellant composition or a manually operated liquid pump to drive the treatment composition. Various types of nebulizers include, but are not limited to: ultrasonic, gas, venturi, nebulizers. Such may be obtained from a variety of commercial sources.

Exemplary nebulizer means which are presently commercially available from Kai-Chih Industrial Ltd. (Taiwan) include those disclosed in one or more of U.S. Pat. No. 6,854,662; a nebulizer and baffle plate assembly as disclosed in U.S. Pat. No. 7,229,029; piezoelectric and percussion board assembly as disclosed in US 2007/0011940; a block piezoelectric actuator and vibratable plate as disclosed in US 2007/0169775; a vibration member comprising a piezoelectric ceramic actuator and a vibratory plate as disclosed in US 2008/00419272, the contents of each of the foregoing being herein incorporated in their entirety by reference. Further nebulizers and/or mist generators include those known to the art, including those disclosed in one or more of the US patents incorporated by reference and discussed in this patent specification.

The mist generator means is energized from the power source and such causes a grid or plate to vibrate at a high frequency and concurrently to emit a cloud of very fine liquid particles, viz., a mist, which may then be omitted. The very fine liquid particles forming the mist of the treatment composition, alternately referred to as a "treatment mist" typically have an average diameter which may be of relatively wide distribution, e.g, from about 0.25 microns to about 500 microns, however it is preferred that the particle size distribution of the fine liquid particles fall within the range of about 5 to about 300 microns, and especially preferably fall in the range of between about 10 to about 100 microns. Preferably the preponderance (>75%, preferably >85%, especially preferably >95%) of the very fine liquid particles forming the mist of the treatment composition is in the range of about 8-80 microns, and especially preferably about 10-50 microns. In certain preferred embodiments, up to about 25%, preferably up to 10% of the very fine liquid particles forming the mist of the treatment composition is in the range of 0.1-10 microns, and up to about 25%, preferably up to 15% of the very fine liquid particles forming the mist of the treatment composition is in excess of 100 microns with the remaining at least 50%, but preferably at least 75% of the very fine liquid particles forming the mist of the treatment composition is in the range of 10-50 microns, and especially preferably in the range of 10-30 microns. Desirably, and in order of increasing preference, not more than about 22%, 20%, 18%, 16%, 15%, 12%, 10%, 9%, 8%, 7%, 6%, 5%, 4%, 3%, 2%, 1% and most preferably essentially none (less than 0.5%) of the very fine liquid particles forming the mist of the treatment composition is in the range of 0.1-10 microns, and concurrently and in order of increasing preference, not more than about 22%, 20%, 18%, 16%, 15%, 12%, 10%, 9%, 8%, 7%, 6%, 5%, 4%, 3%, 2%, 1% and most preferably essentially none (less than 0.5%) of the very fine liquid particles forming the mist of the treatment composition is in excess of 50 microns, with the remaining balance to 100% of the very fine liquid particles forming the mist of the treatment composition within 10 microns and 50 microns.

Alternately wherein the device is intended to deliver a treatment composition which is intended to be respirable or more readily absorbed transdermally then the particle size distribution may be directed to delivering having smaller average diameters than discussed above. In such nebulizers, the mist generator means is energized from the power source and such causes the grid to vibrate at a high frequency and concurrently to emit a cloud of very fine liquid particles, viz., a mist, which may then be omitted. The very fine liquid particles forming the mist of the treatment composition, alternately referred to as a "treatment mist" ("TM") typically have an average diameter which may be of relatively wide distribution, e.g, from about 0.01 microns to about 200 microns, however it is preferred that the particle size distribution of the fine liquid particles fall within the range of about 0.1 to about 50 microns, and especially preferably fall in the range of between about 0.1 to about 25 microns, and particularly preferably from about 0.1 to about 15 microns. Preferably the preponderance (>75%, preferably >85%, especially preferably >95%) of the very fine liquid particles forming the mist of the treatment composition is in the range of 0.1-10 microns. Desirably, and in order of increasing preference, not more than about 22%, 20%, 18%, 16%, 15%, 12%, 10%, 9%, 8%, 7%, 6%, 5%, 4%, 3%, 2%, 1% and most preferably essentially none (less than 0.5%) of the very fine liquid particles forming the mist of the treatment composition are in excess of 10 microns, with the remaining balance to 100% of the very fine liquid particles forming the mist of the treatment composition of 10 microns or less.

In a further preferred embodiment a "bi-modal" distribution of very fine liquid particles are provided by a nebulizer, such that, opposed to many known nebulizers which provide a distribution of very fine liquid particles which are averaged about a median or averaged liquid particle size or liquid particle mass, in said preferred embodiment the nebulizer provides a bi-modal distribution of very fine liquid particles, a first part or proportion of the liquid particles being of a first particle size distribution which are averaged about a first median or first averaged liquid particle size or liquid particle mass, and a second part or proportion of the liquid particles being of a second particle size distribution which are averaged about a second median or second averaged liquid particle size or liquid particle mass. In such embodiments, the average liquid particle size or liquid particle mass of the first median or first particle size distribution is lesser in average or median particle size or mass than the average liquid particle size or liquid particle mass of the second median or second particle size distribution. The provision of such a bi-modal distribution provides for a first part or portion of the liquid particles being of a smaller particle size, preferably having a first median or first averaged liquid particle size in the range of 1-10 microns, preferably 1-8 microns, yet more preferably between 2-7 microns, and a second part or portion of the liquid particles being of a relatively larger particle size, preferably having a second median or second averaged liquid particle size in the range of 10-50 microns, preferably 10-40 microns, yet more preferably between 10-35 microns. Optionally but advantageously, at least 60%, and in order of increasing preference, at least 70%, 75%, 80%, of the particles or mass of the liquid particles present within the first or second proportion are within +/−35% by mass or size, and in order of increasing preference are within "+/−30%, +/−25%, +/−20%, +/−15%, +/−10% of their respective median or average liquid particle size or liquid particle mass. Such provides for a narrowed distribution of the liquid particle sizes or masses delivered by the nebulizer. Further preferably, the mass of the particles delivered in the first part or portion of liquid particles is not more than about ½, preferably not more than about ¼ of the mass of the mass of the particles delivered in the second part or portion of liquid particles, which have a larger average particle size or mass. Alternately, but preferably, the mass ratio of the particles delivered in the first part or portion of liquid particles to the particles delivered in the second part or portion of liquid particles is in the range of about 1:2, and in order of increasing preference is in the respective mass ratio about: 1:3, 1:4, 1:5, 1:6, 1:7, 1:8, 1:9, 1:10. The delivery of the liquid treatment composition as a bi-modal distribution of very fine liquid particles provides for controlled distribution of the treatment composition wherein a controlled mass, but visually very visible amount or mass, of the liquid treatment composition provided in the a first part or proportion of the liquid particles is delivered concurrently with greater mass of the liquid treatment composition provided in the a second part or proportion of the liquid particles. Such minimizes or reduces the amount of treatment composition which is delivered as smaller, potentially respirable liquid droplets or particles in applications and methods of use where it is intended that these be minimized, which said particles are nonetheless airborne and more buoyant than the greater mass of the treatment composition which is delivered as larger, less potentially respirable liquid droplets or particles of the treatment composition.

Mists of the treatment composition, (interchangeably referred to as a treatment mist, TM) has several advantages. A first advantage is that it is flowing and somewhat buoyant, which permits for the deposition of the very fine liquid particles on surfaces which are not necessary adjacent to the outlet of a device from whence the mist is released. This may provide for a small degree of airborne drift and permit for improved deposition of the liquid particles as compared to liquids which may be applied via a manually pumped trigger sprayer, or even liquids dispensed from a pressurized aerosol container. In the case of the former, the droplets of a liquid composition dispensed from a manually pumped trigger sprayer typically have larger average droplet sizes than those delivered by such a mist generator, and hence average droplet masses which concurrently transport and bombard a treated surface with greater amounts of a liquid composition per droplet. Such characteristics minimize the aerial buoyancy of the droplets, and when the droplets contact a surface the greater mass of liquid composition tends to much more quickly wet a surface, primarily by adsorption and to a lesser extent by absorption. Thus, both the larger and heavier particle sizes of the such liquid droplets, and their velocity as they are being released from a manually pumped trigger sprayer typically causes greater amounts of a liquid composition to be dispensed and faster wetting of surfaces. Turning to the latter, delivery of a liquid composition from a pressurized aerosol container typically results in similar delivery characteristics. While a critical selection of the orifice sizes and internal passages of an aerosol canister's spray actuator typically used with such pressurized aerosol container often provides somewhat more selection and control of the average droplet size, still the typical droplets of a liquid composition dispensed from a pressurized aerosol container also typically have larger average particle sizes than those delivered by such a generator, and hence have average droplet masses and greater distribution of average droplet sizes which concurrently transport and bombard a treated surface with greater amounts of a liquid composition per droplet. Such characteristics minimize the aerial buoyancy of the droplets, and when the droplets contact a surface the greater mass of liquid composition tends to much more quickly wet a surface, primarily by adsorption and to a lesser extent by absorption. Further, as the droplets dispensed from a pressurized aerosol container are typically released at a higher linear velocity than even the droplets released from a manually pumped trigger sprayer such even moreso diminishes the likelihood of aerial buoyancy and airborne drift.

The treatment mist emitted from the mist generator in devices according to the invention may provide improved delivery to hard or non-porous surfaces, particularly when such may be associated with articles having three dimensional features, or which themselves have a three-dimensional, e.g., patterned, non-flat planar, or roughened surface. The irregularities in such surfaces may be very effectively treated by providing a mist from a device according to the invention, or according to a process of the invention in the near proximity or adjacent to such a surface, such that the delivered mist is permitted to settle and deposit upon such a three-dimensional surface. The delivery of the mist, which is expected to be airborne for at least a few fractions of a second after being dispensed from a device, will often also exhibit a useful degree of airborne drifting prior to settling upon a treated surface. Such airborne drifting provides for improved coverage of hard surfaces, particularly when such are three-dimensional themselves or are associated with articles having three dimensional features. With regard to the latter, by way of non-limiting example such may be a kitchen countertop or sink from which may extend a plumbing fixture, e.g., a faucet. Another non-limiting example could be a lavatory appliance, e.g. a toilet, bidet, shower, bathtub, or bathroom sink which also includes elements, e.g., faucets, spouts, drains, handles and the like. The airborne drifting of the mist of the treatment composition is also very useful in delivering the treatment composition to open airspace, e.g., a room, a space within the interior of a building, a vehicle cabin or vehicle compartment, as well as within a closed container e.g., the interior of a storage cabinet, a closet, a shower stall, a garbage container or refuse bin, and the like. The delivery of a treatment composition in the form of an airborne mist of the treatment composition, which may be alternately characterized as a cloud of very fine liquid particles of the treatment composition provides for improved surface deposition on such surfaces, including that of such elements. Due to the airborne nature of this mist or cloud, the dispensed mist or cloud forms an enveloping body or penumbra of very fine liquid particles of the treatment composition which may first surround a surface or article, and then deposit thereon by settling of the very fine liquid particles.

Further three-dimensional surfaces which are particularly beneficially treated by the use of a device of the invention or by practice of the inventive process are soft surfaces. Such soft surfaces often exhibit a degree of porosity thus permitting for the passage of gases therethrough. Frequently such also have internal spaces or interstices in their construction. Non-limiting examples of such soft surfaces include: textiles, carpets, garments, and the like. The delivery of a treatment composition via a mist or cloud such as described above typically provides improved penetration of the soft surface due to the drifting of, or penetration of such internal spaces or interstices in a soft surface, e.g., the space between fibers in a twisted yarn, the space between adjacent yarns in the pile or nap of a carpet, the space between fibers of a woven or non-woven textile, such that very fine liquid particles of the treatment composition may be transported into the interior of the soft surface prior to such a particle depositing on a surface. Such an effect might be referred to as an injection of the mist of very fine liquid particles of the treatment composition into the three dimensional matrix of a soft surface wherein at least a part of the emitted very fine liquid particles transit to the interior of the soft surface prior to contacting any part of the soft surface itself, and only thereafter come into contact with and are deposited in the soft surface.

The delivery rates of the devices may vary in order to suit a specific application, e.g., it may be advantageously to have a higher delivery rate of the treatment composition per unit of time (e.g., seconds, minutes, hours, days) for spaces with larger volumes and/or wherein the device is located at a greater distance from the surface or surfaces to be treated, as opposed to closer placement and/or smaller volumes or spaced to be treated. Advantageously the treatment mist dispensed from the device may be delivered at a rate of about 0.5 milliliter/minute to about 100 milliliter/for most applications and uses. Preferably the delivery rate is from about 1-50, more preferably 1-25, still more preferably 1-10 and particularly preferably about 1-5 milliliter/minute.

Optionally but preferably the treatment mist emitted from the mist generator in devices according to the invention may travel along a horizontal surface for a reasonable distance when exiting the device. Preferably the plume of the treatment mist emitted from the mist generator travels up to 60 cm in a lateral or horizontal direction perpendicular to the device, and preferably travels between 1-50 cm in such a direction as measured from where it exits the device. Such permits for the travel, distribution and contact of the treatment mist with surfaces having non-planar geometries, e.g., curved surfaces, as well as travel of the treatment mist to the sides of a surface being treated, including the underside and back sides of a surface being treated.

A further important technical characteristic of the delivery of a treatment composition as an airborne mist of the treatment composition is that typically better surface coverage and a more uniform layer of a treatment composition is deposited on either a hard or soft surface, and thus the actual mass of a treatment composition may be reduced as compared to delivery of the same treatment composition via a manually pumped trigger sprayer or a pressurized aerosol container in order to achieve a comparable technical effect. More simply stated, less of the treatment composition is wasted due to excessive delivery or overspraying than when delivered as a mist or cloud of very fine liquid particles of the treatment composition. Such is beneficial when for example, the delivery of a treatment composition providing a surface cleaning, sanitizing or antimicrobial benefit is desired, or where a film forming polymer is intended to be applied to a surface. In both instances, a more uniform deposition of the treatment composition may be achieved. A further beneficial effect is better noted when delivering a treatment composition to a porous or soft surface, especially a garment or textile. Providing a controlled amount of a treatment composition delivered as a mist or cloud of very fine liquid particles provides for minimization of localized delivery of the composition, e.g., as spots or zones of a treated soft surface which may quickly form a wetted or saturated part of the textile or surface which may result in wrinkling or staining of the area to which a composition has been applied, e.g., such as by a trigger sprayer or from a pressurized aerosol canister. In contrast thereto, the small degree of airborne drift of the treatment composition provided as a mist or cloud of very fine liquid particles provide for a more uniform distribution upon and possibly also within the textile or garment and thus permit for a reduction or minimization of the actual mass of the treatment composition which needs to be provided. Such minimized the likelihood of wetting, saturating, staining or wrinkling of a treated soft surface, especially where such is a garment, or a textile article such as: a carpet surface, rug, window treatment such as curtains or drapes, bedding surfaces including sheets, pillows, blankets, bedspreads, bedcoverings, as well as textiles or articles used in bathrooms, e.g., shower curtains, towels, etc. Attendant upon the use of the device of the invention, a treatment composition which provides a cleaning or odor masking or odor neutralization benefit is delivered as a treatment mist, viz, a cloud of very fine liquid particles which is used to treat a garment or textile article in a sufficient amount in order to provided the desired cleaning or odor masking or odor neutralization benefit. Of course two or more of these benefits may be provided in the practice of the process for treating such soft surfaces.

The device of the invention generates a treatment mist of discrete or aerosolized particles of the treatment composition which is used to treat surfaces, including inanimate hard surfaces and inanimate soft surfaces, as well as topical surfaces. The aerosolized form of a treatment composition comprises at least one treatment agent which ultimately contacts a surface being treated after being dispensed from the device of the invention. The treatment agent may be provided as a constituent of a treatment composition comprising further constituents other than the treatment agent, although a treatment composition consisting solely of a treatment agent is not excluded from the scope of the invention.

The treatment composition comprises at least one treatment agent. The treatment composition provides a technical benefit to a hard surface or soft surface being treated. By way of nonlimiting examples such a technical benefit can be one or more of: a cleaning benefit, a disinfecting benefit, a sanitizing benefit, a bacteriostatic effect, an anti-viral benefit, a sporicidal benefit to reduce the presence of incidence of or regrowth of molds, fungi, spores and the like, an anti-allergen benefit, an anti-acaricidal benefit, an anti-fungal benefit, an anti-resoiling benefit, a limescale removing benefit, a stain removing benefit, an air treatment benefit including but not limited to; fragrancing, odor masking, odor neutralization, an anti-pesticidal benefit, an anti-insecticidal benefit, as well as providing a surface coating to hard surfaces. The treatment composition as applied to hard surfaces and/or soft surfaces may provide a technical benefit which may be transitory or durable, e.g., provide a residual antimicrobial, germicidal or sanitizing benefit such as to reduce the likelihood of the retention, or growth of undesired pathogens (e.g., bacteria, virus, molds) on the treated surface. The treatment compositions may provide a surface coating to hard surfaces and/or to soft surfaces. The treatment composition may also reduce the buildup of biofilms on the treated surface, may reduce the incidence of limescale and/or its buildup after being treated. The treatment composition may provide a surface shine benefit to treated surfaces. The treatment composition may provide an antiresoiling benefit. The treatment composition may deposit a coating on hard surface or soft surface which is hydrophilic in nature or hydrophobic in nature. The treatment composition may provide a surface treatment benefit to improve the tactile benefits thereof, e.g., fabric softening, and the like. The treatment composition may provide an air treatment benefit including but not limited to; fragrancing, odor masking, odor neutralization, air sanitization, an anti-pesticidal benefit, an anti-insectidal benefit. The treatment composition may provide a skin treatment benefit when topically applied to human skin or to any other bodily surface such as hair. The treatment composition may also be a depilatory composition or include a depilatory constituent, e.g., thioglycolic acid, for the removal of hair from the human body. The treatment composition may be an inhalable or respirable composition which comprises a medicament, a vitamin, a pharmaceutical preparation, an edible material and the like. Treatment compositions which are formed into treatment mists necessarily comprise an effective amount of one or more treatment agent within the treatment composition such that the desired technical benefit is provided when the treatment mist is applied to or into a hard surface or soft surface, or supplied in any other means or for any other use.

Prior to being formed into a treatment mist form, the treatment composition is advantageously a flowable liquid at room temperature (20° C.) and at normal atmospheric pressure in which the device of the invention finds use. The viscosity of the treatment composition is not necessarily critical, it only being required that it can be atomized in the device out of the invention and delivered as a mist of comminuted or aerosolized particles. Advantageously however the viscosity of the treatment composition falls within the range of about 0-2000 cP, preferably between about 0.5-1000 cP, and especially preferably between about 0.5-500 cP. Especially preferred embodiments of the treatment composition are free flowable liquids, i.e. are "water thin" and thus are readily flowable, as well as being readily pumpable either by mechanical means such as by a pump, or by capillary means such as within a narrow diameter tube, and which is also readily easily and effectively atomized by the mist generator means.

Advantageously, the treatment composition includes a large proportion, that is to say at least about 50% wt. of a liquid. In certain preferred embodiments the treatment composition is at least 60% wt., and in order of increasing preference, 70% wt., 80% wt., 90% wt., 95% wt. 97% wt., 98% wt., 99% wt. and to 100% wt. of a liquid. The liquid is preferably a free-flowing liquid at room temperature and normal prevailing atmospheric conditions as noted above. Advantageously, the liquid may be water, or may be one or more non-aqueous solvents, e.g., one or more organic solvents, or may be a mixture or composition comprising both water and one or more further non-aqeuous solvents, e.g., one or more organic solvents. The water may be tap water, but is preferably distilled and is most preferably deionized water. By way of non-limiting example exemplary useful organic solvents which may be included in the treatment compositions include those which are at least partially water-miscible such as alcohols (e.g., low molecular weight alcohols, such as, for example, ethanol, propanol, isopropanol, and the like), glycols (such as, for example, ethylene glycol, propylene glycol, hexylene glycol, and the like), water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethylene glycol or propylene glycol (e.g. propylene glycol monomethyl ether acetate), and mixtures thereof. Of course, mixtures of two or more organic solvents may be used concurrently. One preferred organic solvent which may be included within the treatment compositions is triethylene glycol which is believed to provide odor sanitization or odor neutralizing benefits to an airspace within which culminated particles of triethylene glycol are present. Thus in such certain embodiments where such a technical benefit is desired, the inclusion of triethylene glycol may be considered for its advantageous benefit. When present, it can be included in amounts effective to provide a desired degree of air sanitization. In certain embodiments it is also expressly contemplated that triethylene glycol is the preponderant constituent present, or even the sole treatment agent present in a treatment composition.

The treatment composition may also include one or more surfactants. The presence of one or more such surfactants which are advantageously included to typically provide for the loosening of soils or other hydrophobic matter which may be present on a surface being treated with the device of the invention. Such surfactants may be selected from one or more of anionic, nonionic, cationic, amphoteric and zwitterionic surfactants. Such are per se, known to the art. Non-limiting examples of anionic surfactants include sulfates and sulfonates of organic compounds, e.g., alkyl compounds. Further non-limiting examples of anionic surfactants include alkyl carboxylates, alkyl ether carboxylates, sulfosuccinates, taurates, alkyl phosphates, isethionates, alkylpolysaccharide sulfates, alkylpolyglucoside sulfates, sarcosinates or mixtures thereof. Anionic soaps may also be used in the inventive compositions. Examples of the foregoing anionic surfactants are available under the following tradenames: Rhodapon®, Stepanol®, Hostapur®, Surfine®, Sandopan®, and Biosoft® tradenames.

Exemplary useful nonionic surfactants are those which include a hydrophobic base portion, such as a long chain alkyl group or an alkylated aryl group, and a hydrophilic chain portion comprising a sufficient number of ethoxy and/or propoxy moieties to render the nonionic surfactant at least partially soluble or dispersible in water. By way of non-limiting example, such nonionic surfactants include ethoxylated alkylphenols, alkoxylated fatty alcohols, polyethylene glycol ethers of methyl glucose, polyethylene glycol ethers of sorbitol, ethylene oxidepropylene oxide block copolymers, ethoxylated esters of fatty ($C_6$-$C_{24}$) acids, condensation products of ethylene oxide with long chain amines or amides, condensates of alkylene oxides, particularly ethylene oxide with sorbitan fatty acid esters, e.g., polyoxyethylene sorbitan monolaurate, polyoxyethylene sorbitan monopalmitate, polyoxyethylene sorbitan trioleates, alkoxylated alkanolamides, e.g. $C_8$-$C_{24}$ alkyl di($C_2$-$C_3$ alkanol amide) as well as mixtures thereof. Examples of the useful nonionic surfactants include materials are available under the Tomadol®, Neodol®, Rhodasurf®, Genapol®, Pluronic®, Lutensol®, Emulgen® and Alfonic® tradenames. Further useful nonionic surfactants include alkylmonoglycosides and alkylpolyglycosides are prepared generally by reacting a monosaccharide, or a compound hydrolyzable to a monosaccharide with an alcohol such as a fatty alcohol in an acid medium; examples include D-glucopyranoside, available as Glucopon® 625 CS which is described as being a 50% $C_{10}$-$C_{16}$, alkyl polyglycoside.

The treatment compositions may include one or more amphoteric surfactants, non-limiting examples of which are: derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., a carboxy, sulfonate, or a sulfate group, such as sodium 3-(dodecylamino)propionate, and sodium 3-(dodecylamino)propane-1-sulfonate, sarcosinates, taurates, amide sulfosuccinates, and betaines including phosphobetaines. Exemplary betaines include dodecyl dimethyl betaine, cetyl dimethyl betaine, and dodecyl amidopropyldimethyl betaine.

The treatment composition may also comprise one or more cationic surfactant constituents, especially preferably one cationic surfactants which provide an appreciable germicidal benefit. Non-limiting examples of preferred cationic surfactant compositions which may be included in the treatment compositions are those which provide an appreciable germicidal benefit, and especially preferred are quaternary ammonium compounds and salts thereof, which may be characterized by the general structural formula:

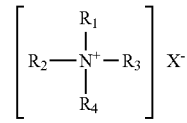

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility or water miscibility of the quaternary ammonium complex. Preferred quaternary ammonium compounds which act as germicides according to the foregoing formula are those in which $R_2$ and $R_3$ are the same or different $C_8$-$C_{12}$alkyl, or $R_2$ is $C_{12-16}$alkyl, $C_{8-18}$ alkylethoxy, $C_{8-18}$alkylphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Such useful quaternary compounds are available under the BARDAC®, BARQUAT®, HYAMINE®, LONZABAC®, and ONYXIDE® trademarks When one or more cationic surfactants which provide an appreciable germicidal benefit are present, they may be present as a co-antimicrobial agent, with a further antimicrobial agent described hereinafter. When one or more cationic surfactants which provide an appreciable germicidal benefit are present, preferably anionic surfactants and further optionally, amphoteric surfactants are omitted from the treatment compositions of the invention. Other surfactants, although not specifically disclosed herein but known to the art may also be used within the treatment compositions of the present invention.

The treatment of the compositions may also include one or more fluorosurfactants, non-limiting examples of which include the anionic salts of perfluoroaliphaticoxybenzene sulfonic acids and the anionic salts of linear perfluoroalkyloxybenzoic acids/Other suitable fluorocarbon surfactants are compounds according to the following structures and descriptions:
- (a) $R_fCH_2CH_2SCH_2CO_2M$ wherein $R_f$ is $F(CF_2CF_2)_n$ and n is from about 3 to about 8 and M is alkali metal (e.g., sodium or potassium) or ammonium;
- (b) $C_nF_{2n+1}SO_3M$ wherein $C_nF_{2n+1}$ is a straight chain fluorocarbon radical, n is from about 8 to about 12 and M is alkali metal or ammonium;
- (c) $C_nF_{2n+1}SO_3M$ wherein $C_nF_{2n+1}$ is a straight chain fluorocarbon radical, n is from about 8 to about 12 and M is an alkali metal cation;
- (d) $R_fCH_2CH_2O(CH_2CH_2O)_nH$ wherein $R_f$ is a straight chain $F(CF_2CF_2)_n$ radical and n is from about 3 to about 8;
- (e) $R_f(OCH_2CH_2)_nOR_f$ wherein $R_f$ is a branched chain radical of the formula $C_8F_{15+}C_{10}F_{19}$ or $C_{12}F_{23}$ and n is from about 10 to about 30; and
- (f) $R_f(OCH_2CH_2)_mOR$ wherein $R_f$ is a branched chain radical of the formula $C_8F_{15+}C_{10}F_{19}$ or $C_{12}F_{23}$, m is from about 2 to about 20 and R is $C_1$ to $C_3$ alkyl.

Fluorinated hydrocarbon surfactants are available from numerous commercial sources as trademarked products. Examples are ZONYL fluorosurfactants from E.I. duPont de Nemours & Co., FLUORAD fluorosurfactants from 3M Company, e.g., FLUORAD FC-129 ($R_fSO_2N(C_2H_5)CH_2CO_2^-K^+$, where $R_f$ is $C_nF_{2n+1}$ and n is about 8), The treatment compositions may comprise further antimicrobial agents other than the one or more cationic surfactants described above. Such an antimicrobial agent is/are one or more compounds other than cationic surfactants which provide an appreciable germicidal benefit, viz., cationic germicide, described above. Such an antimicrobial agent desirably provides an effective antimicrobial benefit to a treated surface, other than a cationic germicide, preferably such that the treatment composition delivered by the device of the invention exhibits at least 3 $\log_{10}$ kill efficacy, preferably at least 4 $\log_{10}$ kill efficacy at 60 seconds contact time of at least two, preferably at least three and most preferably at least four of microorganisms selected from the group consisting of: *S. aureus, E. coli, P. aeruginosa* and *E. hirae*, desirably according accepted and standardized testing protocols for the evaluation of antimicrobial efficacy of a composition applied to a hard surface, soft surface, or a dermal surface, i.e. a human or animal epidermis.

The antimicrobial agent may include one or more of: pyrithiones such as zinc pyrithione, halohydantoins such as dimethyldimethylol hydantoin, methylchloroisothiazolinone/methylisothiazolinone sodium sulfite, sodium bisulfite, imidazolidinyl urea, diazolidinyl urea, benzyl alcohol, 2-bromo-2-nitropropane-1,3-diol, formalin (formaldehyde), iodopropenyl butylcarbamate, chloroacetamide, methanamine, methyldibromonitrile glutaronitrile, glutaraldehyde, 5-bromo-5-nitro-1,3-dioxane, phenethyl alcohol, o-phenylphenol/sodium o-phenylphenol, sodium hydroxymethylglycinate, polymethoxy bicyclic oxazolidine, dimethoxane, thimersal dichlorobenzyl alcohol, captan, chlorphenenesin, dichlorophene, chlorbutanol, glyceryl laurate, halogenated diphenyl ethers such as 2,4,4-trichloro-2-hydroxy-diphenyl ether (Triclosan®) and 2,2-dihydroxy-5,5-dibromo-diphenyl ether, phenolic antimicrobial compounds such as mono- and poly-alkyl and aromatic halophenols, such as p-chlorophenol, methyl p-chlorophenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, and 5-chloro-2-hydroxydiphenylmethane, resorcinol and its derivatives, bisphenolic compounds such as 2,2-methylene bis(4-chlorophenol) and bis(2-hydroxy-5-chlorobenzyl)sulphide, benzoic esters (parabens), halogenated carbanilides such as 3-trifluoromethyl-4,4'-dichlorocarbanilide (Triclocarban), 3-trifluoromethyl-4,4-dichlorocarbanilide and 3,3,4-trichlorocarbanilide.

The antimicrobial agent may include one or more of: biguanides such as polyhexamethylene biguanide, p-chlorophenyl biguanide; 4-chlorobenzhydryl biguanide, 1,6-bis-(4-chlorobenzylbiguanido)-hexane (Fluorhexidine®), halogenated hexidine including, but not limited to, chlorhexidine (1,1'-hexamethylene-bis-5-(4-chlorophenyl biguanide) (Chlorhexidine®), as well as salts of any of the foregoing, e.g. polyhexamethylene biguanide hydrochloride.

The treatment compositions of the invention may also comprise one or more organic or inorganic acids which may be used to adjust the pH of the treatment composition to a target range or level, and/or to impart an antimicrobial benefit. The acids may be one or more of a water soluble inorganic acids, mineral acids, or organic acids, with virtually all such known materials contemplated as being useful in the treatment compositions. By way of non-limiting example useful inorganic acids include mineral acids, hydrochloric acid, phosphoric acid, sulfuric acid, and the like.

In certain embodiments, the inventive compositions comprise one or more organic acids which may be used to adjust the pH of the treatment composition, and which optionally may also provide an antimicrobial benefit. Exemplary organic acids are those which generally include at least one carbon atom, and include at least one carboxyl group (—COOH) in its structure. Derivatives of said organic acids are also contemplated to be useful. Exemplary organic acid include linear aliphatic acids such as acetic acid; dicarboxylic acids, acidic amino acids, and hydroxy acids such as glycolic acid, lactic acid, hydroxyacrylic acid, alpha-hydroxybutyric acid, glyceric acid, malic acid, tartaric acid and citric acid, as well as acid salts of these organic acids. Of these, citric acid, sorbic acid, acetic acid, boric acid, formic acid, maleic acid, adipic acid, lactic acid, malic acid, malonic acid, glycolic acid, salicylic acid and/or derivatives thereof, e.g., salicylic acid derivatives such as esters of salicylic acid, such as ethylhexyl salicylate, dipropylene glycol salicylate, TEA salicylate, salicylic acid 2-ethylhexylester, salicylic acid 4-isopropyl benzylester, salicylic acid homomenthylester are preferred. Of course mixtures of one or more acids are contemplated as being useful.

The treatment composition may comprise a peroxygen compound which may be essentially any compound containing a dioxygen (O—O) bond. Dioxygen bonds, particularly bivalent O—O bonds, are readily cleavable, thereby allowing compounds containing them to act as powerful oxidizers. Non-limiting examples of classes of peroxygen compounds include peracids, peracid salts, and peroxides such as hydrogen peroxide. The peroxygen can be any aliphatic or aromatic peracid (or peroxyacid) that is functional for disinfectant purposes in accordance with embodiments of the present invention. While any functional peroxyacid can be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid. Exemplary peracid salts include permanganates, perborates, perchlorates, peracetates, percarbonates, persulphates, and the like. Exemplary peroxide compounds include hydrogen peroxide, metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith are also considered to be a source of hydrogen peroxide, thereby producing hydrogen peroxide in situ.

The treatment compositions of the invention may also include an oxidizing agent which may be a halogen bleach. Preferably, the oxidizing agent is a halogen bleach source which may be selected from various hypohalite-producing species, for example, bleaches selected from the group consisting of the alkali metal and alkaline earth salts of hypohalite, haloamines, haloimines, haloimides and haloamides. All of these are believed to produce hypohalous bleaching species in situ. Preferably, the oxidizing agent is a hypohalite or a hypohalite generator capable of generating hypohalous bleaching species. Hereafter, the term "hypohalite" is used to describe both a hypohalite or a hypohalite generator, unless otherwise indicated. Preferably, the hypohalite oxidizing agent is a hypochlorite or a generator of hypochlorite in aqueous solution, although hypobromite or a hypobromite generator is also suitable. Representative hypochlorite generators include sodium, potassium, lithium, magnesium and calcium hypochlorite, chlorinated trisodium phosphate dodecahydrate, potassium and sodium dichloroisocyanurate and trichlorocyanuric acid. Organic bleach sources suitable for use include heterocyclic N-bromo and N-chloro imides such as trichlorocyanuric and tribromocyanuric acid, dibromocyanuric acid and dichlorocyanuric acid, and potassium and sodium salts thereof, N-brominated and N-chlorinated succinimide, malonimide, phthalimide and naphthalimide. Also suitable are hydantoins, such as dibromodimethyl-hydantoin and dichlorodimethyl-hydantoin, chlorodimethylhydantoin, N-chlorosulfamide(haloamide) and chloramine(haloamine). When present, advantageously the hypohalite oxidizing agent is an alkali metal hypochlorite, an alkaline earth salt of hypochlorite, or a mixture thereof.

The treatment composition of the invention may include a treatment agent which provides an anti-static or surface softening benefit to a surface, particularly a textile or fibrous surface being treated. Coming into consideration as treatment agents for providing a fiber, textile or fabric softening benefit are one or more compounds which are known to the art as fabric softener compounds. By way of non-limiting example such include all the current commercial quaternary long-chain softeners, and preferably at least partially unsaturated esterquats. Exemplary suitable fabric softeners include fabric softening compounds which are cationic, water insoluble quaternary ammonium compounds comprising a polar head group and two long hydrocarbyl moieties, preferably selected from alkyl, alkenyl and mixtures thereof, wherein each such hydrocarbyl moiety has an average chain length equal to or greater than $C_{12}$, preferably greater than $C_{14}$, more preferably greater than $C_{16}$. More preferably still, at least 50% of each long chain alkyl or alkenyl group is predominantly linear. A preferred overall chain length is about $C_{18}$, though mixtures of chain lengths having non-zero proportions of lower, e.g., $C_{14}$, $C_{16}$ and some higher, e.g., $C_{20}$ chains may be desired.

The cationic softener can suitably be distearyl dimethyl ammonium chloride or unsaturated analogs thereof, but preferably the selected quaternary ammonium fabric softener is biodegradable. Such a property is common to many commercial esterquat fabric softeners such as di(tallowyloxyethyl) dimethyl ammonium chloride. In a preferred embodiment, the fabric softening compound is a quaternary ammonium esterquat compound having two $C_{12-22}$ alkyl or alkenyl groups connected to a quaternary ammonium moiety via at least one ester moiety, preferably two such ester moieties. Of course mixtures of two or more fabric softener compounds.

The treatment compositions of the invention may also include a treatment agent which provides an air treatment technical benefit. By way of nonlimiting examples, such include fragrances, perfumes, compositions for the control or eradication of airborne insects, odor neutralizing agents, odor masking agents, as well as those which may impart holistic or aromatherapy benefits.

A fragrance may form part of the treatment composition, and which may be based on natural and synthetic fragrances and most commonly are mixtures or blends of a plurality of such fragrances, optionally in conjunction with a carrier such as an organic solvent or a mixture of organic solvents in which the fragrances are dissolved, suspended or dispersed. When present such a fragrance constituent may be present in the treatment composition in any effective amount. Advantageously, the fragrance or perfume is present in amounts of from about 0.00001% wt. to about 50% wt. based on the total weight of the treatment composition of which they form a part, although, due to the mode of delivery of the mist generator means to which does not impart thermal degradation of such a constituent, its inclusion in even higher amounts to about 100% wt. of the treatment composition are also contemplated as being possible and indeed advantageous in certain embodiments of the invention.

The treatment composition of the invention may include one or more holistic constituents, particularly may include one or more essential oils which are selected to provide a so-called "aromatherapy benefit" to the user. Such essential oils are frequently extracted from naturally occurring botanical sources such as flowers, stems, leaves, roots and barks of aromatic plants. Similarly to fragrance compositions which may also include one or more essential oils, frequently, due to their potency, essential oils are often supplied dispersed in a liquid carrier such as in one or more organic solvents in which the essential oils are dissolved or dispersed. Preferred essential oils providing an aromatherapy benefit include one or more selected from chamomile oil, lavendin oil, lavender oil, grapefruit oil, lemon oil, line oil, mandarin orange oil, orange flower oil and orange oil. When present, these one or more essential oils providing an aromatherapy benefit are present in any effective amount, advantageously are present in amounts of from about 0.00001% wt. to about 50% wt. based on the total weight of the treatment composition of which they form a part, although, due to the mode of delivery of the mist generator means to which does not impart thermal degradation of such a holistic constituent or essential oils, their inclusion in even higher amounts to about 100% wt. of the treatment composition are also contemplated as being possible and indeed advantageous in certain embodiments of the invention. It is to be understood that these one or more essential oils providing an aromatherapy benefit may be used with our without the optional fragrancing constituent recited previously and alternately, may be used wholly or partially in place of said fragrancing constituent.

To maintain or establish a desired pH of a treatment composition, the use of one or more pH buffers is contemplated.

The treatment compositions according to the invention optionally but desirably include an amount of a pH adjusting agent or pH buffer composition. Such compositions include many which are known to the art and which are conventionally used. By way of non-limiting example pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts.

Desirably the compositions according to the invention include an effective amount of an organic acid and/or an inorganic salt form thereof which may be used to adjust and maintain the pH of the treatment compositions of the invention to the desired pH range.

The treatment compositions of the invention may also include one or more alkanolamines which in addition to providing an improved cleaning benefit may also be used to concurrently adjust the pH of the treatment composition. By way of nonlimiting examples such include monoalkanolamines, dialkanolamines, trialkanolamines, and alkylalkanolamines such as alkyl-dialkanolamines, and dialkyl-monoalkanolamines. The alkanol and alkyl groups are generally short to medium chain length, that is, from 1 to 7 carbons in length. For di- and trialkanolamines and dialkyl-monoalkanolamines, these groups can be combined on the same amine to produce for example, methylethylhydroxypropylhydroxylamine. One of skill can readily ascertain other members of this group.

The treatment compositions of the invention may also comprise one or more hydrotropes, preferably one or more anionic hydrotrope compounds. Exemplary hydrotropes include, e.g., benzene sulfonates, naphthalene sulfonates, $C_1$-$C_{11}$ alkyl benzene sulfonates, naphthalene sulfonates, $C_5$-$C_{11}$ alkyl sulfonates, $C_6$-$C_{11}$ alkyl sulfates, alkyl diphenyloxide disulfonates, and phosphate ester hydrotropes. Particularly useful hydrotrope compounds include benzene sulfonates, o-toluene sulfonates, m-toluene sulfonates, and p-toluene sulfonates; 2,3-xylene sulfonates, 2,4-xylene sulfonates, and 4,6-xylene sulfonates; cumene sulfonates, wherein such exemplary hydrotropes are generally in a salt form thereof, including sodium and potassium salt forms.

According to a further aspect of the invention, there is provided a method for the treatment of hard surfaces and soft surfaces which method comprises the step of providing a device which generates a mist of a treatment composition, which treatment composition contacts the surface and provides a technical benefit thereto.

According to an additional aspect of the invention, there is provided a method for the treatment of inanimate, nonporous hard surfaces which method comprises the step of providing a device which generates a mist of a treatment composition, which mist contacts said hard surfaces and provides a technical benefit thereto. Typically, the technical benefits provided are one or more of: cleaning benefit, a disinfecting benefit, a sanitizing benefit, a bacteriostatic effect, an antiviral benefit, a sporicidal benefit to reduce the presence of, incidence of or regrowth of molds, fungi, spores and the like, an anti-allergen benefit, an anti-acaricidal benefit, an antifungal benefit, an anti-resoiling benefit, a surface treatment benefit to improve the appearance thereof, e.g., surface shine and the like, an air treatment benefit including but not limited to; fragrancing, odor masking, odor neutralization, air sanitization, an anti-pesticidal benefit, an anti-insectidal benefit as well as providing a surface coating to hard surfaces. By way of non-limiting example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry, as well as flooring surfaces, e.g., wood, tile, glass, ceramic, cement surfaces, grout, linoleum, carpets, rugs, and the like.

According to a further aspect of the invention, there is provided a method for the treatment of soft surfaces, e.g., fabrics, textiles, garments, and the like which method comprises the step of providing a device which generates a mist of a treatment composition, which treatment composition contacts the aforementioned fabrics, textiles, garments, and the like and which optionally further also penetrates the surface or services thereof, and which provides a technical benefit thereto. Similar to the above, the treatment compositions delivered by the device according to this method may comprise one or more solvents such as water and/or organic solvents, and one or more further constituents especially one or more surfactants or other materials which provide a disinfecting, sanitizing, or antimicrobial benefits to the treated surfaces. Typically, the technical benefits provided are one or more of: fragrancing, perfuming, odor neutralizing, malodor treating or masking, cleaning, sanitization, disinfection, textile or fabric softening, antiwrinkling such as of garments or textiles, as well as providing a treatment or a coating of a film forming composition to the treated soft surface, e.g, application of a fluoropolymer surfactant containing treatment composition to particularly to resist subsequent staining of such treated surfaces, including garments, textiles, upholstery, carpeted surfaces, rugs, as well as threads and fibers used in the production of such soft surfaces, and the like.

According to a yet further aspect of the invention, there is provided a method for controlling the incidence of dust mites, and or controlling their residual fecal matter, as well as denaturation of allergens, e.g., "der-p" and "der-f" allergens, which method comprises the step of providing a device which generates a mist of a treatment composition, which treatment composition contacts the surface and provides a technical benefit thereto. The treatment compositions delivered by the device according to this method comprise typically may comprise one or more solvents such as water and/or organic solvents, and one or more further constituents especially one or more of: organic acids and in particular lactic acid, citric acid, surfactants, essential oils and enzymes.

According to a further aspect of the invention there is provided a method for the treatment of medical instruments, e.g., surgical instruments, dental instruments, or other instruments to be used in medical procedures which come into direct contact with parts of the human body and which require periodic cleaning, disinfection, sanitization or sterilization which method comprises the step of providing a device which generates a mist of a treatment composition, which treatment composition contacts said medical instruments and provides a cleaning, disinfection, sanitization or sterilization benefit to the treated medical instruments.

In a still further aspect of the invention there is provided a method for the delivery of an air treatment composition to an airspace, which method comprises the step of providing a device which generates a mist of a treatment composition, which treatment composition contacts said airspace and provides a technical benefit thereto. Typically, the technical benefits provided are one or more of: fragrancing, perfuming, odor neutralizing, malodor treating or masking, air sanitization. The treatment compositions delivered by the device according to this method comprise one or more solvents such as water and/or organic solvents, and one or more further constituents.

In a yet further aspect of the invention there is provided a method for the pre-treatment or post-treatment of an article to be treated in a laundry machine for the cleaning treatment, e.g., dry cleaning, or laundering treatment, e.g., aqueous laundering of fabrics, textiles, garments, and the like which method comprises the step of providing a device which generates a mist of a treatment composition, which composition contacts the aforementioned fabrics, textiles, garments, and the like and which optionally further also penetrates the surface or services thereof, and which provides a technical benefit thereto.

In a further aspect of the invention there is provided a method for the delivery of an air treatment composition to an enclosed airspace, which method comprises the step of providing a device which generates a mist of a treatment composition, which treatment composition contacts said enclosed airspace and provides a technical benefit thereto, e.g., fragrancing, perfuming, odor masking, malodour neutralization, air sanitization, and the like. Examples of such enclosed airspaces include larger or open airspaces, e.g., a larger volumes such as a room, public space within the interior of a building, a cabin or compartment within a vehicle, as well as within a closed container or other relatively smaller space, e.g., the interior of a storage cabinet, a closet, a shower stall, a garbage container or refuse bin, and the like. The delivery of a mist of a treatment composition which provides a fragrancing, odor masking, perfuming, odor neutralization, disinfecting, sanitizing, or other technical benefit to the interior of a container for collecting and storing wastes, garbage or refuse, including rigid containers such as cans, drums, bins, baskets and the like or flexible containers such as bags, envelopes and the like is a contemplated and preferred embodiment of the invention.

According to a further aspect of the invention there is provided a method for the pre-treatment or post-treatment of an article, such as a dishware article, to be treated in an dishwashing process, e.g., a manual dishwashing process, or in an automatic dishwashing machine, which method comprises the step of providing a device which generates a mist of a treatment composition, which said composition contacts dishware e.g., tableware, glassware, cooking utensils, cookware, and the like, and which provides a technical benefit thereto. Typically, the treatment compositions delivered by the device according to this method comprise one or more solvents such as water and/or organic solvents, and one or more further constituents especially one or more surfactants or other materials which provide a disinfecting, sanitizing, or antimicrobial benefits to the treated surfaces. Typically, the technical benefits provided are one or more of: cleaning, sanitization, disinfection, surface treatment, such as by providing a coating of a film forming composition to the treated hard surface particularly to resist subsequent staining of such treated surfaces.

According to a still further aspect of the invention, there is provided a method for the application of a treatment composition to a bodily surface, e.g., a dermal surface, or hair surface, which method comprises the step of providing a device which generates a mist of a treatment composition which composition contacts the bodily surface and provides a technical benefit thereto. Exemplary bodily surfaces include the epidermis, e.g., hands, arms, legs, face, scalp as well as other body areas. Typically, the treatment compositions delivered by the device according to this method comprise one or more solvents such as water and/or organic solvents, and one or more further constituents especially one or more surfactants or other materials which provide a disinfecting, sanitizing, antimicrobial benefits, deodorization, fragrancing, perfuming, skin nourishment, skin conditioning, wound treatment benefit to the treated bodily surfaces. In a preferred method, an anti-acne or skin cleansing composition is applied to a bodily surface, preferably to skin surfaces of the head, face and neck, in order to provide a treatment composition which may provide an anti-acne or skin cleansing benefit. A treatment composition providing an anti-acne benefit may comprise an effective amount of salicylic acid or other anti-acne active constituent or composition which may remediate the incidence thereof.

In a yet further aspect of the invention there is provided a method for the delivery of a depilatory composition to a skin upon which hair growth may be present, which method includes the step of supplying a depilatory composition or a composition containing a depilatory constituent, e.g. thioglycolic acid, to the skin surface.

In a still further aspect of the invention there is provided a method for the delivery of a nebulized or atomized fluid treatment composition, viz., treatment mist to a surface, or to an enclosed cavity, volume, or space. By way of nonlimiting examples, such enclosed interiors, cavity, volume, or other enclosed space include a way of example: body cavities, e.g., buccal cavity; the enclosed interior of rooms, buildings and the like; being closed interior of vehicles such as cars, buses, trucks, aircraft, boats and ships and the like; the enclosed interior of the storage lockers, cabinets, closets, boxes and the like.

In a yet further aspect the present invention provides a device and a method for the delivery of a mist of a treatment composition which provides a pesticidal, mitocidal, viricidal, antimicrobial or sanitizing benefit by delivery of a mist of a treatment composition from the device of a nebulized or atomized fluid treatment composition which treatment composition comprises one or more constituents which provide a pesticidal, mitocidal, viricidal, antimicrobial or sanitizing benefit.

Reference is now made to the drawings, which illustrate various embodiments of the invention, including certain preferred embodiments of the invention. In the accompanying figures, like elements are indicated using like numerals throughout the figures.

FIG. 1 depicts an embodiment of a mist generator means 20 which comprises a vibrating plate 22, here formed of a microperforated metal screen or sheet having a plurality of microperforations 21 passing therethrough. The vibrating plate 22 is generally circular, and includes a peripheral piezoelectric element 24. Although depicted in the embodiment that the piezoelectric element is at the peripheral edge 26 of the vibrating plate 22 and is affixed thereto, it is to be understood that the piezoelectric element 24 may be affixed to any part of the vibrating plate 22 and is not necessarily required to be at the periphery thereof. Further illustrated on the figure are a pair of electrical current carrying means 40, or, namely a pair of wires which supply an electrical current from the circuit control means (not shown) which acts to operate the mist generator means 20 by inducing the vibrations within that the vibrating plate 22 which acts to pump the mist TM of the treatment composition from the vibrating plate 22 as is indicated by reference arrows labeled "TM".

FIG. 2 depicts an alternative embodiment of a mist generator means 20 which also comprises a vibrating plate 22, however in the present embodiment to series of segments 23 pass through the vibrating plate. Reference is made to U.S. Pat. No. 7,229,028, the entire contents of which are herein incorporated by reference, which also illustrates such elements. Similarly, a piezoelectric element 24 is similarly illustrated at the peripheral age 26 of the vibrating plate 22 and is likewise affixed to thereto. Also illustrated is current carrying means 40, namely a pair of wires are also illustrated for providing means to transmit an electrical current to the piezoelectric element 24 from the circuit control means (not shown) to induce vibrations within the mist generator means 20 so to pump a treatment composition in the form of a mist TM in the direction of the reference arrows TM.

Figure 6:
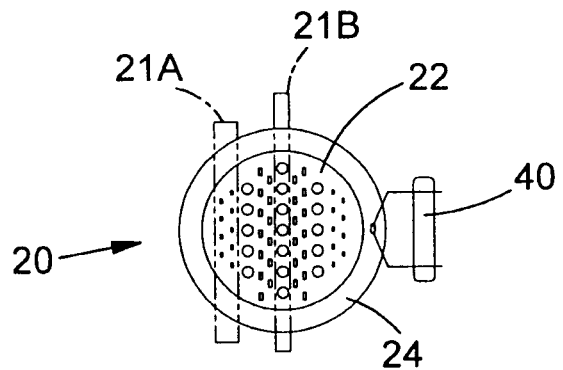
FIG. 6 depicts an embodiment of a mist generator means.
Figure 7:
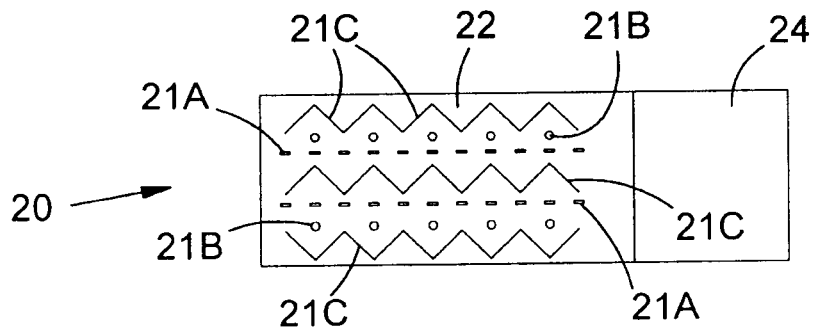
FIG. 7 depicts an embodiment of a mist generator means.
Figure 8:
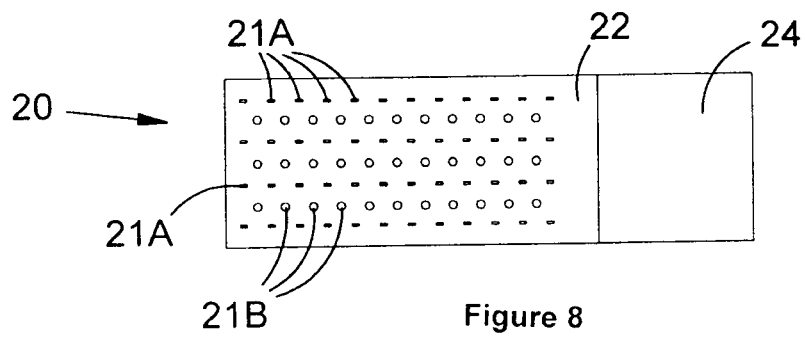
FIG. 8 depicts an embodiment of a mist generator means.

FIGS. 6, 7 and 8 depict embodiments of a mist generator means 20 of different configurations which are adapted to provide a bi-modal distribution of liquid droplets or particles, viz., a treatment mist of the treatment composition. The embodiment presented on FIG. 6 is similar in most respects to the embodiments according to FIGS. 1 and 2, but differ in that the vibrating plate 22 formed of a micro-perforated metal screen or sheet comprises a first series of microperforations 21A passing therethrough and a second series of microperforations 21B passing therethrough, which are of different configurations or sizes, e.g., cross section or diameters, the microperforations of each series being of different configurations or sizes, e.g., cross section or diameters than those of the other or different series. Treatment composition being nebulized by the mist generator means 20 is provided as a treatment mist having a bi-modal distribution of liquid droplets or liquid particles. The embodiment of FIG. 7 illustrates a further embodiment of a mist generator means 20 having a rectangular configuration, and includes a vibrating plate 22 formed of a micro-perforated metal screen or sheet comprises a first series of microperforations 21A passing therethrough, a second series of microperforations 21B passing therethrough, and a third series of microperforations 21C passing therethrough, the microperforations of each series being of different configurations or sizes, e.g., cross section or diameters than those of another series; treatment composition being nebulized by the mist generator means 20 is provided as a treatment mist having a three-modal distribution of liquid droplets or liquid particles. The embodiment of FIG. 8 illustrates a further embodiment of a mist generator means 20 having a rectangular configuration, and includes a vibrating plate 22 formed of a micro-perforated metal screen or sheet comprises a first series of microperforations 21A passing therethrough, and a second series of microperforations 21B passing therethrough; the microperforations of each series being of different configurations or sizes, e.g., cross section or diameters than those of another series; treatment composition being nebulized by the mist generator means 20 is provided as a treatment mist having a bi-modal distribution of liquid droplets or liquid particles.

It is to be understood however the in many useful embodiments the mist generator means 20 comprises a vibrating plate 22 which includes only a single series of microperforations 21 passing therethrough which are all similarly sized, such as in the embodiments illustrated in FIGS. 1 and 2, which depict eminently suitable mist generator means 20 which may be used in any embodiment of the invention, and which provide a treatment mist TM having a unimodal particle distribution.

FIGS. 3, 4 and 6 illustrate in a more detailed, cross-sectional view the operation of a portion of a vibrating plate 22 under normal operating conditions. Typically, when an appropriate electrical current is passed through the piezoelectric element 24, such induces the configuration, or the expansion and contraction of the piezoelectric element 24. The vibrating plate 22, at least a part of which is mechanically, chemically, or otherwise physically bonded to at least a part of the piezoelectric element 24 similarly vibrates but to due to the more flexible nature of the vibrating plate 22, an oscillatory pattern is introduced in to the vibrating plate 22. Where the vibrating plate 22 is generally circular in nature and is bound on its periphery to the piezoelectric element 24, as is disclosed in FIGS. 1 and 2, typically a rippling waveform, which extends from the periphery and towards the center of the vibrating plate 22 manifests itself. However when the vibrating plate 22 is generally rectangular, or is bonded on only one of its sides or one of its ends to piezoelectric element 24, a typically rippling waveform which extends from the point of connection between vibrating plate 22 and the piezoelectric 24 is manifested. The latter is due to the fact that wherein the parts of the vibrating plate 22 are not mechanically bound, such provides for more freedom of movement of the vibrating plate 22 at such points thereon. Nonetheless, in such a configuration, the waveform induces flexure of the vibrating plate 22 such that during the passage of a wave, or part of a waveform across any point of the vibrating plate 22, the region surrounding such a point will bend either upwardly, or downwardly with respect to the same point, as compared to the condition of the same point when the vibrating plate 22 is in a static state. FIGS. 3, 4 and 6 illustrates a cross-sectional view of a small section of a vibrating plate 22 in various states of operation. FIG. 3 illustrates a cross-sectional view of a small section of a vibrating plate 22 in such a static state. As is visible thereon, the vibrating plate 22 includes a series of microperforations or channels 25 passing therethrough, which optionally but preferably have a slightly wider diameter or width of channel entries 25a at the bottom face 22a of the vibrating plate 22, and slightly narrower diameter or width of channel exits 25b at the top face 22b of the vibrating plate 22. Such is believed to improve the pumping action of the treatment composition being transferred through the vibrating plate 22 when it operates as part of the mist generator means 20. Turning now to FIG. 4, the same portion of the vibrating plate 22 is illustrated in the condition as being a "trough" of a portion of the waveform during the oscillation of the vibrating plate 22. Depicted are also pair of microdroplets "MD" of the treatment composition which are present at the passage entries 25a at the bottom face 22a of the vibrating plate 22. Such for example may be formed by the presence of a treatment composition beneath the vibrating plate 22, such as when supplied in a liquid form. Turning now to FIG. 5, the same portion of the vibrating plate 22 is illustrated in the condition as it being at a "peak" of a portion of the waveform during the oscillation of the vibrating plate 22. As is visible thereon, the direction of flexure of the vibrating plate is now reversed with respect to that as illustrated on FIG. 5, and as it is in an outwardly bowed direction perspective thereto, the passage exits 25b have a somewhat increased width or diameter as compared to one of the vibrating plate 22 was in the trough position, via., as per FIG. 4 or even when in a static position, as per FIG. 3. Concurrently, the diameter or width of the passage entries 25a at the bottom face 22a of the vibrating plate 22 are reduced as compared to one of the vibrating plate 22 was in the trough position, via., as per FIG. 4 or even when in a static position, as per FIG. 3, and such causes the microdroplets MD of the treatment composition to be expelled outwardly from the vibrating plate 22 in the direction of reference arrows TC. In such a manner, pumping of a liquid composition, here the treatment composition of the invention can be achieved across the thickness of the vibrating plate 22.

It is however to be noted that while the provision of pumping across the thickness of the vibrating plate 22 provides an excellent means of atomizing the treatment composition and thereby providing a treatment composition in a form of a mist, it is foreseen that the treatment composition can alternately be supplied directly to the top face 22b of the vibrating plate 22, and due to the vibratory oscillation of the vibrating plates 22, microdroplets MD of the treatment composition are also formed without necessarily passing through the vibrating plate 22 as described immediately above.

Figure 9:
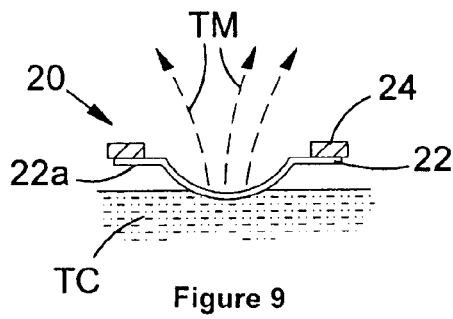
FIG. 9 depicts an embodiment of a mist generator means.

FIG. 9 depicts a further embodiment of a vibrating plate 22 forming part of a mist generator means 20 of the invention, similar in several respects to the embodiments illustrated on FIGS. 1 and 2. Thereupon is illustrated a mist generator means 20 which comprises a vibrating plate 22, here formed of a bowl shaped micro-perforated metal screen or sheet. The vibrating plate 22 is generally circular, and includes a peripheral piezoelectric element 24. A portion of the bottom face 22a is in contact with the surface of, or is partially immersed with the treatment composition TC, here in the form of a liquid. When operating, the mist generator means 20 pumps microdroplets of the treatment composition outwardly from the interior of the bowl shaped vibrating plate 22, upwardly an outwardly in the direction of reference arrows TM.

Figure 10:
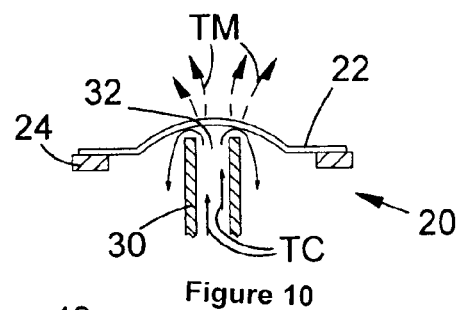
FIG. 10 depicts an embodiment of a mist generator means.

FIG. 10 depicts a further embodiment of a mist generator means 20 according to the invention. In the depicted in embodiment, there is provided a vibrating plate 22, here formed of a bowl shaped micro-perforated metal screen or sheet which is generally circular and includes a peripheral piezoelectric element 24. A portion of the bottom face 22a is in contact with a surface of, or partially immersed with the treatment composition TC, here in the form of a column of flowing liquid supplied by a fluid conduit 30, here a circular tube. The treatment composition TC flows out from the open end 32 of the tube 30 and maintains a meniscus or layer of the treatment composition at this open end 32. When operating, the mist generator means 20 pumps microdroplets of the treatment composition as a treatment mist outwardly from the interior of the bowl shaped vibrating plate 22, upwardly and outwardly in the direction of reference arrows TM, as during part of its oscillation, the vibrating plate 22 comes into contact with the treatment composition TC and pumps it through and outwardly from the vibrating plate 22 in the manner described previously. The quantity of the treatment composition which exits the tube 30 can be recirculated to resupply the vibrating plate 22 or alternately, can be collected or drained off and discarded. In this manner, by control of the operating characteristics of the mist generator means 20, and the rate at which the treatment composition TC is supplied, the use of a capillary or wick as a fluid transport means can be omitted or excluded from the device.

Figure 11:
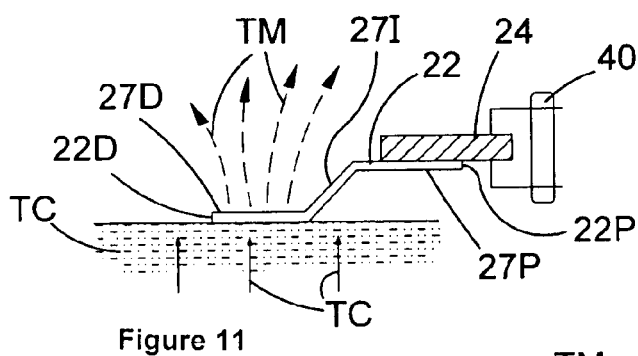
FIG. 11 depicts an embodiment of a mist generator means.

FIG. 11 depicts an alternative embodiment of a mist generator means 20 according to the invention. The mist generator means 20 comprises a piezoelectric element 24 and a vibrating plate 22, here formed of a micro-perforated metal screen or sheet which is generally rectangular in configuration. In the present embodiment, only one end of the vibrating plate 22 on bonded to piezoelectric element 24, and during operation of the mist generator means 20 a typically rippling waveform which extends from the a proximal end 22P of the vibrating plate 22 along its length to its distal end 22D, is manifested. The latter is due to the fact that as parts of the vibrating plate 22 are not mechanically bound, particularly in the distal end 22D such provides for more freedom of movement of the vibrating plate 22. In the illustrated embodiment, while the vibrating plate 22 is generally rectangular it also is bent thus to define 3 interconnected parts, a proximal end part 27D, an intermediate part 27I, and a distal end part 27D. In the depicted embodiment, the proximal end part 27P and distal end part 27D all are generally parallel but spaced apart from one another via the intermediate part 27I which is angled to both the proximal end part 27D and distal end part 27D. Here, the angles are approximately equal and approximately between 30 and 45 degrees of arc. Greater, and lesser angles are contemplated than the angles shown in the figure. Further illustrated on the figure are a pair of electrical current carrying means 40, or, namely a pair of wires which supply an electrical current from controller means (not shown) which acts to operate the mist generator means 20 by inducing the vibrations within that the vibrating plate 22 which acts to pump the treatment composition outwardly from vibrating plate 22 as is indicated by reference arrows "TM". As illustrated in this figure, the distal end part 27D of the vibrating plate 22 is in contact with, or immersed in a quantity of the treatment composition TC, here present in the form of a liquid. Although not visible in the drawings, the distal end part 27D includes passages or microperforations as discussed with reference to FIG. 1, 2, 6, 7 or 8. During operation of the mist generator means 20, oscillation of the vibrating plate 22 pumps microdroplets of the treatment composition outwardly from the vibrating plate 22, in the direction of reference arrows TM. The particle size distribution in the treatment mist TM may be a unimodal distribution, a bimodal distribution, a trimodal distribution or any other distribution.

Figure 12:
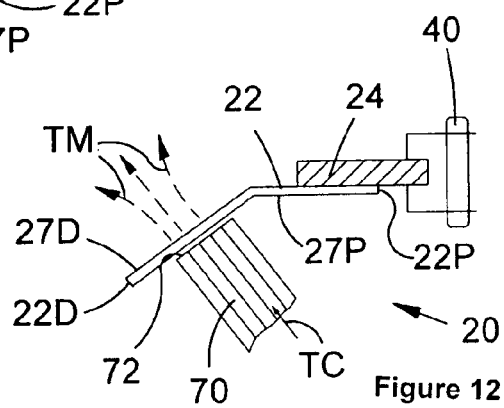
FIG. 12 depicts an embodiment of a mist generator means.

FIG. 12 illustrates a further embodiment of a mist generator means 20 similar in some respects to the embodiment depicted on FIG. 11. In the present figure, a portion of a rectangular vibrating plate 22 is affixed, attached or bonded to a piezoelectric element 24, and the rectangular vibrating plate 22 extends outwardly therefrom. The vibrating plate 22 has a proximal end part 27P which extends via an intermediate angle to a distal end part 27D which comprises passages or microperforations as discussed with reference to FIGS. 1 and 2. Thus the portion of the vibrating plate 22 comprising passages or microperforations is inclined. The treatment composition in the form of a liquid is supplied by a capillary means 70 here depicted as a bundle of narrow diameter tubes 70 which transfer the treatment composition towards the terminal end 72 of the tubes 70 from a reservoir containing the treatment composition (not shown). Most preferably the tubes 70 are a plurality of thin diameter tubes wherein delivery of the treatment composition to the terminal end 72 thereof may be due to capillary forces within each fo the thin diameter tubes, or the transport and delivery of the treatment composition may be due to a pump forcing the treatment composition through the tubes 70 and to the terminal end 72. During operation, a film layer or meniscus at the terminal end 72 of the treatment composition is formed, and during part of its vibratory motion the vibrating plate 22 contacts the film layer or meniscus of the treatment composition and entrains it. During the vibratory movement of the vibrating plate 22, the portion of the vibrating plate 22 comprising the passages or microperforations entrains, and thereafter pumps the treatment composition through the vibrating plate 22 upward and outward from the vibrating plate 22 in the direction of reference arrows TM.

Figure 13:
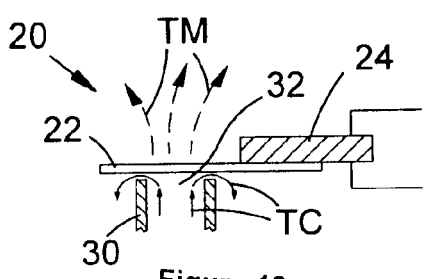
FIG. 13 depicts an embodiment of a mist generator means.
Figure 14:
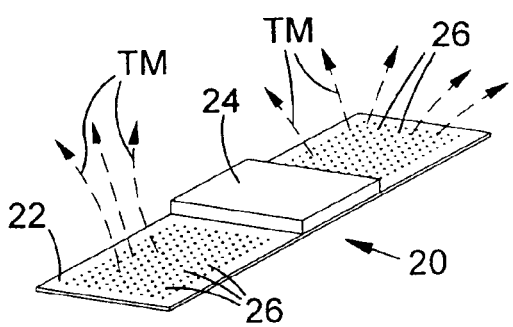
FIG. 14 depicts an embodiment of a mist generator means.

FIG. 13 depicts an embodiment of a part of mist generator means 20 wherein a treatment composition TC is supplied to the vibrating plate 22 as a column of flowing liquid supplied by a fluid conduit 30, here a circular tube, and wherein a sufficient amount of the treatment composition is present at the open end of the fluid conduit 30 and any excess treatment composition TC may overflow. During part of its oscillation, the vibrating plate 22 comes into contact with the treatment composition TC and pumps it through and then outwardly from the vibrating plate 22 and in the direction of reference arrows TM FIG. 14 depicts an embodiment of a mist generator means 20 adapted for use with dual sources of the treatment composition. As is visible thereon, a vibrating plate 22 of a generally rectangular configuration comprises a piezoelectric element 24 in its midsection. The vibrating plate 22 has two distal end parts 27D each of which comprises passages or microperforations as discussed with reference to FIGS. 1 and 2, 6, 7 and 8.

Figure 15:
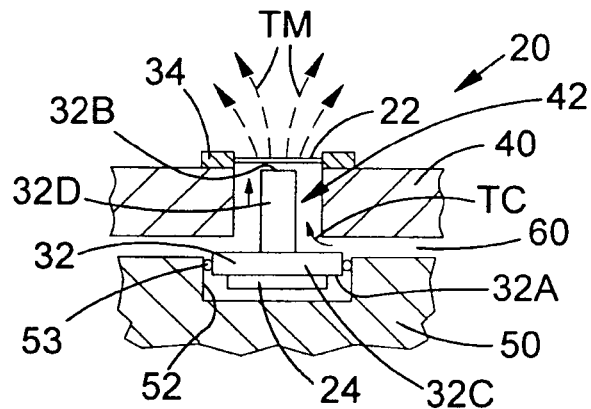
FIG. 15 depicts a further embodiment of a mist generator means.

FIG. 15 depicts a further alternative form of the mist generator means 20 useful devices of the invention. A vibrating plate 22 which is bonded, mounted, or otherwise affixed to a peripheral piezoelectric element 24 generally is depicted in either of FIG. 1 or 2, is positioned slightly above the base 44 of a weir 43 present within a first body part 40 of the device. A fluid conduit 60 supplies a quantity of the treatment composition TC to the top face 22b of the vibrating plate 22. A small gap may exist between the bottom face 22a of the vibrating plate 22 and the base 44 thereby defining a base cavity 46. When the piezoelectric element 24 is actuated, the vibratory motion within the vibrating plate 22 causes the formation of a mist TM of atomized particles of the treatment composition TC within the atomizing chamber 45 which are expelled therefrom. Thus, the figure illustrates that the treatment composition TC need not necessarily be pumped through the vibrating plate in order to atomize the treatment composition TC. Advantageously, any liquid or fluid treatment composition TC which may collect within this base cavity 46 was ultimately atomized by the vibratory motion within the vibrating plate 22 which also exits the atomizing chamber 45.

Figure 16:
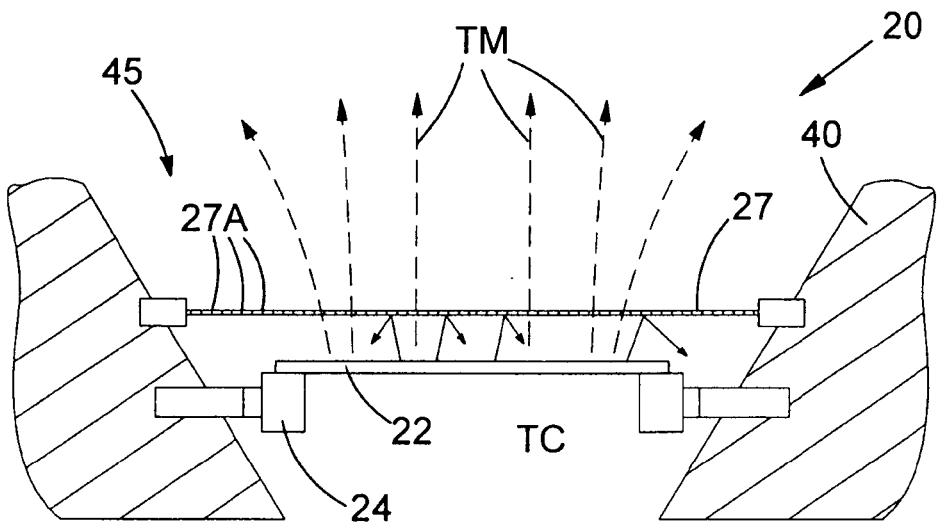
FIG. 16 illustrates a further embodiment of a mist generator means.

FIG. 16 illustrates a further embodiment of a mist generator means 20 useful in devices of the invention. A vibrating plate 22 which however only optionally but preferably includes microperforations 21, 25 passing therethrough as described with reference to FIGS. 1, 2, 6, 7 and 8, is bonded, mounted, or otherwise affixed to a peripheral piezoelectric element 24 generally is depicted in either of FIG. 1 or 2 is positioned within an atomizing chamber 45 transversing the weir 43. Parallel and spaced apart from the vibrating plate 22 is a perforated screen element 27 having a plurality of perforations 21 passing therethrough. In operation, the vibrating plate 22 operates to nebulize the treatment composition into discrete droplets or particles which are directed towards the perforated screen element 27, however only those discrete droplets or particles not in excess of a specific droplet size or particle mass are expelled as a treatment mist TM, while the those discrete droplets or particles TC in excess of a specific droplet size or particle mass are returned to the vibrating plate 22. In this manner a controlled maximum particle size for the discrete droplets or particles of the treatment mist may be established.

In the embodiments disclosed in FIGS. 10 and 11, a bore, cavity or other configuration other than a weir with at least one sloping sidewall may be used as part of the atomizing chamber 45 as disclosed in several of the following figures.

Figure 17:
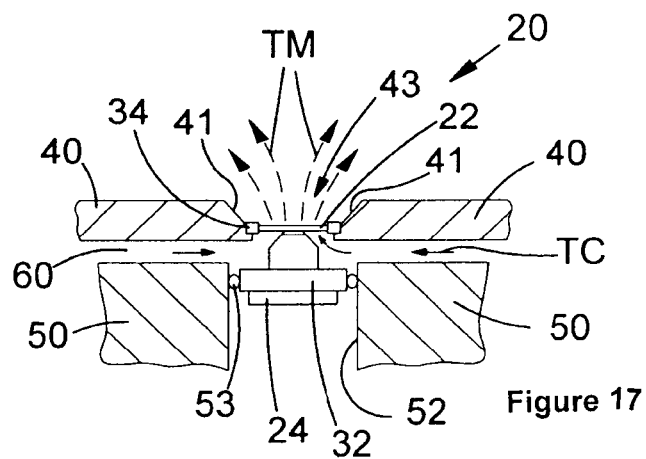
FIG. 17 depicts an atomizing chamber present within a first body part of a mist generator means.

With reference now to FIG. 17, therein is depicted a further embodiment of an atomizing chamber 45 present within the first body part 40A, here a generally circular bore 42 having a base 44 opposite from an open and 48. Above the slightly concave shaped base 44 and mounted transversely across a portion of the bore 42 is a vibrating plate 22 and a piezoelectric element 24 as depicted on FIG. 4. A supply of the treatment composition TC enters the atomizing chamber 45 via fluid conduit and above the vibrating plate 22 such that it contacts the top face 22b. When the piezoelectric element is actuated, vibrations are induced within the vibrating plate 22 which causes the formation of a mist TM of atomized particles of the treatment composition TC within the atomizing chamber 45 which are expelled via the open end 48. Any liquid or fluid treatment composition TC which may collect between the vibrating plate 22 and the slightly concave shaped base 44 is also atomized by the vibratory motion within the vibrating plate 22 and also exits the atomizing chamber 45. FIG. 26 also illustrates a sensor means, here a mist sensor means. In the instant embodiment the mist sensor means 71, includes a transmitter unit 71A and a receiver unit 71A mounted transversely from each other across the bore 45 and preferably near the open end 48 thereof. The transmitter unit generates a signals, e.g. such as optical, acoustic, or other signal capable of being received by the receiver unit, and any variations in the quality of the signal being transmitted due to the quantity or quality of the presence of the atomized particles, viz, mist, of the treatment composition passing through the gap between the transmitter unit 71A and receiver unit 72B, as represented by arrow 73 is detected by the receiver unit. An appropriate signal can be transmitted to the controller means (not shown) which may initiate a responsive action by the controller means and one or more further parts of the device. For example, wherein the mist sensor means determines that an insufficient quantity of the atomized particles of the treatment composition are being produced, a signal representative of this state may be transmitted to the controller means which for example may increase the power or alternately increase the frequency signal being transmitted to the piezoelectric elements 24 to thereby increase the rate of its oscillation or vibration, and/or alternately the mass flow rate of the treatment composition TC, such as may be supplied via a pump, may be increased. Alternately, the mist sensor means may also determine if the atomizing chamber 45 is flooded with the fluid form of the treatment composition and upon sending a signal to the control unit representative thereof, the control unit may cause an appropriate response, e.g., shutting down of the device or interrupting the operation of the mist generator 20. Still alternately, the mist sensor means may also determine the absence or presence of the mist of the treatment composition within the atomizing chamber 45, and if the latter is sensed then a representative signal may be sent to the control unit may cause an appropriate response, e.g., shutting down of the device or interrupting operation of the mist generator 20.

Although not illustrated in the depictions, it is to be understood nonetheless that suitable electrical or signal unit conducting means, i.e. wires, may be used to connect the various elements of the mist sensor means, the fluid control means, the controller means, as well as any other device, elements or parts of the device as may be required, although such is not necessarily illustrated in the figures presented herein.

FIGS. 18 and 19 illustrate by means of graphical representations preferred treatment mist particle size or particle mass bi-modal distributions. Figure A1 represents the mass distribution or % distribution of the size (in microns) of the discrete liquid droplets being dispensed by a mist generator, during normal steady state operation over a convenient time interval, e.g., 1 or more seconds, or one or more minutes. As is seen thereon, a greater amount of particles in the range of 0-10 microns are dispensed than the amount of particles in the range of 10-20 microns, whereas the amount of particles in the successive ranges of 20-30 microns is greater than those dispensed in the prior two ranges. As particle sizes increase to higher ranges, viz., 30-40 microns, and 40-50 microns, their amounts decrease successively. As can also be seen from FIG. 18, the total mass of the dispensed particles in the range of 0-10, is substantially lesser than the total mass of the dispensed particles in the ranges of 20 microns and greater. FIG. 19 illustrates two further alternative bi-modal distributions according to preferred embodiments of the invention, here represented as a first bi-modal distribution represented by "C1" (in solid line) and a second bi-modal distribution represented by "C2" (in dotted line). The curves represent the distribution, by % wt. or mass or percentage of respective discrete liquid droplets or particles of the treatment composition present in a treatment mist formed therefrom, as indicated on the y-axis, for droplets within a particular micron size range, as indicated on the x-axis. With reference to line C1, it is seen that the first median or first averaged liquid particle size corresponds to line segment C11, which is approximately at 4 microns with the particle size distribution within the first part of the bi-modal distribution being beneath the curved line C1 to the left and right of the line segment C11, and the second median or second averaged liquid particle size corresponds to line segment C12, which is at approximately 29 microns, with the particle size distribution within the second part of the bi-modal distribution being to the left and right of the line segment and beneath curved line C1. The further bi-modal distribution represented by C2 is similar in many respects but, first median or first averaged liquid particle size corresponds to line segment C21, which is approximately at 5 microns with the particle size distribution within the first part of the bi-modal distribution being beneath the curved line C2 to the left and right of the line segment C21, and the second median or second averaged liquid particle size corresponds to line segment C22, which is at approximately 22 microns, with the particle size distribution within the second part of the bi-modal distribution being to the left and right of the line segment and beneath curved line C2.

FIGS. 20 and 21 depict a preferred embodiment of a mist generator assembly 400 comprising a mist generator means 20 which includes a vibrating plate 22 affixed, bonded to or otherwise mounted on a peripheral piezoelectric element similar in most respects to embodiments discussed with reference to FIGS. 1, 2, 6, and/or 9 although other mist generator means not specifically disclosed may be adapted for use. In the depicted embodiment, the mist generator assembly 400 includes a first body element 40A having an open end 48 across which spans and is mounted the mist generator means 20, here wherein the peripheral edge 26 of the piezoelectric element 24 is mounted within the bore 42 of the first body element 40A and defines an atomizing chamber 45, and which also defines a base cavity 46 within the first body element 40A rearward or inwardly of the mist generator means 20. The mist generator means 20 is mounted to the first body element 40A in a liquid, seal-tight manner. Further illustrated on the figure are a pair of electrical current carrying means 40, or, namely a pair of wires which supply an electrical current from the circuit control means (not shown) which acts to operate the mist generator means 20 by inducing the vibrations within that the vibrating plate 22 which acts to pump the mist of the treatment composition TM from the mist generator assembly 400; the means 40 (wires) may pass through a part of the first body element 40A via a suitable perforation or channel or pathway or for that matter by any other suitable arrangement of the elements of the mist generator assembly 400. There is also present a fluid conduit 30 which has an open end 32 which extends into the base cavity 46 via a supply bore 31 into which the treatment composition TC is provided from the fluid conduit 30 by any suitable means, e.g., capillary flow, gravity flow but most preferably via pump intermediate the reservoir of the treatment composition and the mist generator assembly 400. In a preferred mode of operation the controller means is operated to control the volumetric flow rate of the pump means used to supply the treatment composition to the base cavity 46, as well as concurrently controlling the operation of the mist generator means 20 and its output such that a satisfactory delivery rate of the treatment mist TM is generated, and concurrently a sufficient amount of the treatment composition TC is supplied to the mist generator assembly 400 such that the an ample supply of the TC is present therein, but at the same time pumping of an excess of the treatment composition TC and "flooding" of the base cavity 46 is desirably avoided.

While the first body element 40A may be formed or fabricated from any suitable material, such as a metal, synthetic polymer, ceramic material, and the like advantageously at least the part of the first body element 40A of the mist generator assembly 400 to which the mist generator means 20 is fixed is at least elastomeric or partially elastomeric in nature. This permits for the mist generator means 20 is mounted to both provide a liquid tight seal with the first body element 40A and to permit for the motion of the vibrating plate, and further denies passage of any treatment composition present within the base cavity 46 to exit the mist generator assembly 400 except through the microperforations 21 of the screen 22. The advantage of such construction allows for the mist generator assembly 400 used in any variety of orientations as will be described in greater detail in later figures. Wherein at least part of the first body element 40A is flexible or elastomeric at least at the region of the interface between the mist generator means 20 and the first body element 40A, such permits for the easy installation or mounting of the mist generator means 20 when the region of the interface between the mist generator means 20 and the first body element 40A can be stretched or distended to permit for the installation of the mist generator means 20, and when the region is permitted to return to its original orientation, a liquid-tight seal is formed between the first body element 40A and the mist generator means 20. In certain particularly preferred embodiments, the first body element 40A of the mist generator assembly 400 and be constructed or formed of a monolithic mass of an elastomeric material such as a rubber, silicone, or other flexible material which can simultaneously be used to mount and retain the mist generator means 20 in the manner depicted. Preferably parts of, or all of the first body element 40A also acts to absorb vibratory shocks emanating from the operating mist generator means 20 to other parts of the device, and/or to be felt by the user of the device. In certain preferred embodiments the first body element 40A is wholly formed of a flexible or elastomeric material.

A further embodiment of a mist generator means is depicted in FIG. 25, which is similar in most respects to the embodiment illustrated in FIGS. 20 and 21. The embodiment of FIG. 25 differs primarily in that the mist generator assembly 400 is formed of a conjoined first body element 40A and a second body element 40B via set of mating screw threads 40S. Intermediate the first body element 40A and the second body element 40B is positioned the mist generator means 20, which includes a vibrating plate 22 affixed, bonded to or otherwise mounted on a peripheral piezoelectric element similar in most respects to embodiments discussed with reference to FIGS. 1, 2, 6, and/or 9 although other mist generator means not specifically disclosed may be adapted for use. Herein the material of construction of the first body element 40A and the second body element 40B is not necessarily an elastomeric or flexible material but is depicted to be a rigid material. Such a rigid material can be for example a ceramic, metal, but is advantageously a synthetic polymer which can be easily injection molded, shape, or otherwise formed, and which is also nonporous thereby useful in retaining the treatment composition TC within its interior, especially within the base cavity 46. The first body element 40A has a horn-shaped or cone-shaped open end 48 across which spans and is mounted the mist generator means 20, here wherein the peripheral edge 26 of the piezoelectric element 24 is mounted between two elastomeric sealing members, here illustrated as two O-rings, 40R1 and 40R2 which provide a liquid tight seal between the mist generator means 20 and the first body element 40A and the second body element 40B when they are assembled. In such manner, the mist generator means 20 is mounted to the first body element 40A in a liquid, seal-tight manner via the two elastomeric sealing members. This positioning also defines an atomizing chamber 45 forwardly or outwardly of the mist generator means 20, and which also defines a base cavity 46 within the second body element 40B rearward or inwardly of the mist generator means 20. Not shown though understood to be present are a pair of electrical current carrying means 40, or, namely a pair of wires which supply an electrical current from the circuit control means (not shown) which acts to operate the mist generator means 20 by inducing the vibrations within that the vibrating plate 22 which acts to pump the mist of the treatment composition TM from the mist generator assembly 400; the means 40 (wires) may pass through a part of the first body element 40A and/or second body element 40B via a suitable perforation or channel or pathway or for that matter by any other suitable arrangement of the elements of the mist generator assembly 400. As visible from this side cross-sectional view, there is also present a fluid conduit 30 which has an open end 32 which extends into the base cavity 46 via a supply bore 31 into which the treatment composition TC is provided from the fluid conduit 30 by any suitable means, e.g., gravity flow but most preferably via a pump intermediate the reservoir of the treatment composition and the mist generator assembly 400. In a preferred mode of operation the controller means is operated to control the volumetric flow rate of the pump means used to supply the treatment composition to the base cavity 46, as well as concurrently controlling the operation of the mist generator means 20 and its output such that a satisfactory delivery rate of the treatment mist TM is generated, and concurrently a sufficient amount of the treatment composition TC is supplied to the mist generator assembly 400 such that the an ample supply of the TC is present therein, but at the same time pumping of an excess of the treatment composition TC and "flooding" of the base cavity 46 is desirably avoided.

A further embodiment of a mist generator means is depicted in FIG. 26, which is similar in most respects to the embodiment illustrated in FIGS. 20, 21 and 25. The embodiment of FIG. 26 differs primarily in that the mist generator assembly 400 is formed of a conjoined first body element 40A and a second body element 40B via compression-type fitting therebetween which is facilitated as in this preferred embodiment the first body element 40A is formed of a flexible elastomeric material. The first body element 40A functions as a mounting frame for the mist generator means 20, which includes a vibrating plate 22 affixed, bonded to or otherwise mounted on a peripheral piezoelectric element similar in most respects to embodiments discussed with reference to FIGS. 1, 2, 6, and/or 9 although other mist generator means not specifically disclosed in this figure may be adapted for use. Herein the material of construction of the second body element 40B is not necessarily an elastomeric or flexible material but is depicted to be a rigid material. Advantageously the rigid material is a synthetic polymer which can be easily injection molded, shape, or otherwise formed, and which is also nonporous thereby useful in retaining the treatment composition TC within its interior, especially within the base cavity 46. The first body element 40A has a horn-shaped or cone-shaped open end 48 across which spans and is mounted the mist generator means 20, here wherein the peripheral edge 26 of the piezoelectric element 24 is mounted within a circumferential recess 40R which encases the peripheral edge 26 and which provides a liquid tight seal therebetween. The first body element 40A also forms a liquid tight seal with the second body element 40B when these elements are assembled. Advantageously, as shown in the figure, the first body element 40A includes a sloping exterior sidewall 40AF which extends at least into the region exterior of the a circumferential recess 40R which encases the peripheral edge 26 and the second body element 40B includes a corresponding sloping interior sidewall 40BF which comes into contact with the first body element 40A. Preferably the dimensions of the first body element 40A and the second body element 40B are such that a slight compression is imparted to the first body element 40A when it is inserted into the second body element 40B such that the former is seeded into the latter and forms a liquid tight seal there with and simultaneously compressive forces exist within the first body element and particularly in the region of the circumferential recess 40R which functions to both seat and seal the mist generator means 20 therein. In such manner, the mist generator means 20 is mounted to the first body element 40A in a liquid, seal-tight manner with in the mist generator assembly 400. This positioning also defines an atomizing chamber 45 forwardly or outwardly of the mist generator means 20, and which also defines a base cavity 46 within the second body element 40B rearward or inwardly of the mist generator means 20. Not shown though understood to be present are a pair of electrical current carrying means 40, or, namely a pair of wires which supply an electrical current from the circuit control means (also not shown) which acts to operate the mist generator means 20 by inducing the vibrations within that the vibrating plate 22 which acts to pump the mist of the treatment composition TM from the mist generator assembly 400; the electrical current carrying means 40 (e.g., wires) may pass through a part of the first body element 40A and/or second body element 40B via a suitable perforation or channel or pathway or for that matter by any other suitable arrangement of the elements of the mist generator assembly 400. As visible from this side cross-sectional view, there is also present a fluid conduit 30 which has an open end 32 which extends into the base cavity 46 via a supply bore 31 into which the treatment composition TC is provided from the fluid conduit 30 by any suitable means, e.g., gravity flow but most preferably via a pump intermediate the reservoir of the treatment composition and the mist generator assembly 400. Further this woman figure is an overflow conduit 46C which extends into the base cavity 46, and had shown is connected to an overflow tube 47T which may be used to further direct the exiting treatment composition TC away from the mist generator assembly 400. In a preferred mode of operation the controller means is operated to control the volumetric flow rate of a pump means used to supply the treatment composition to the base cavity 46, as well as concurrently controlling the operation of the mist generator means 20 and its output such that a satisfactory delivery rate of the treatment mist TM is generated, and concurrently a sufficient amount of the treatment composition TC is supplied to the mist generator assembly 400 such that the an ample supply of the TC is present therein, but at the same time pumping of an excess of the treatment composition TC and "flooding" of the base cavity 46 is desirably avoided. However should excess treatment composition TC be present within the mist generator assembly 400 and particular within the base cavity 46, such excess treatment composition TC can be withdrawn and removed via the overflow tube 47T.

FIGS. 22, 23 and 24 illustrate in several views a further preferred embodiment of a mist generator assembly 400 which includes many of the features discussed with reference to prior FIGS. 20, 21, 25 and 26. Turning to the cross-sectional depiction provided by FIG. 22, as depicted the mist generator assembly 400 includes a first body element 40A having an open end 48 across which spans and is mounted the mist generator means 20, here wherein the peripheral edge 26 of the piezoelectric element 24 is mounted within the bore 42 of the first body element 40A and defines an atomizing chamber 45, and also defines a base cavity 46 within the first body element 40A and rearward of the mist generator means 20. The mist generator means 20 is mounted to the first body element 40A in a liquid, seal-tight manner. Further illustrated are a pair of electrical current carrying means 40, e.g., a pair of wires which supply an electrical current from the circuit control means (not shown) which acts to operate the mist generator means 20 by inducing the vibrations within that the vibrating plate 22 which acts to pump the mist TM of the treatment composition from the mist generator assembly 400; the means 40 (wires) may pass through a part of the first body element 40A via a suitable perforation, or may otherwise pass outwardly from the mist generator assembly 400 by any other path. For the present within the illustrated embodiment there is also provided a trough 46T within the first body element 40A extending from the base cavity 46 inwardly, that is to say in a direction away from the mist generator means 20 within which, when the mist generator assembly 400 is fully or partially inverted, some of the treatment composition TC may collect within the trough 46T. Optionally, but preferably as shown in the embodiments of FIGS. 22, 23 the mist generator assembly 400 further comprises an overflow conduit 46C which is in fluid communication with the trough 46T such that, any of the treatment composition TC which may be present within the trough 46T may be drawn off, or otherwise exit the mist generator assembly 400 therethrough. Advantageously, the overflow conduit 46C is further connected to a suitable overflow tube 47T which may be used to further direct the exiting treatment composition TC away from the mist generator assembly 400. A fluid conduit 30 having an open end 32 extends into the base cavity 46 of the mist generator assembly 400 into which the treatment composition TC is provided via the said fluid conduit 30 by any suitable means, e.g., capillary flow, gravity flow but again, most preferably is supplied via a pump or pumps intermediate the reservoir of the treatment composition and the mist generator assembly 400. Preferably the controller means is operated to control the volumetric flow rate of the pump means used to supply the treatment composition to the base cavity 46, of the mist generator assembly 400 as well as concurrently controlling the operation of the mist generator means 20 and its output such that a satisfactory delivery rate of the treatment mist TM is generated, and concurrently a sufficient amount of the treatment composition TC is supplied to the mist generator assembly 400 such that the an ample supply of the TC is present therein, but at the same time pumping of an excess of the treatment composition TC and "flooding" of the base cavity 46 is desirably avoided. In the present embodiment the risk of undesirable flooding of the said device is usually avoided by the action of the overflow conduit 46C connected to the trough 46T, as any excess of the treatment composition TC entering the base cavity 46 at an excessive volumetric flow rate can be shunted away and out from the mist generator assembly 400. FIG. 23 illustrates a bottom plan view of the mist generator assembly 400 illustrating the arrangement of the mist generator means 20, the plate 22 including microperforations or passages 21 passing therethrough, the mist generator means 20 mounted within the bore 42 at the peripheral edges 26 of the plate. FIG. 24 illustrates in a perspective view, the base of the mist generator assembly 400, albeit with the depiction of the mist generator means 20 removed for the purposes of clarity in this figure. As visible there from, the trough 46T is concentric and extends around the supply bore 31 through which the treatment composition TC been provided from the fluid conduit 30 passes into the base cavity 46.

FIGS. 27, 28, and 29 depict a mist generator assembly 400 generally as described with reference to FIG. 22 in three different modes of operation of the vibrating plate 22 of the mist generator means 20. In these figures, the mist generator assembly 400 is oriented with respect to the horizontal, which is represented by line "H". In the first of the figures, in FIG. 27 there is illustrated a quantity of treatment composition TC as represented by the labeled arrows supplied via the fluid conduit 30 into the base cavity 46. The rate of delivery of the treatment composition TC is controlled such that the volume of the treatment composition TC present within the base cavity 46 does not fill it, and a headspace "HS" above the treatment composition TC within the base cavity 46 is present. The vibrating plate 22 is extended outwardly as shown, and particles of the treatment mist TM are generated. In the next of the figures, in FIG. 28, the vibrating plate 22 of the mist generator means 20 is at its intermediate position. In the last of the figures, in FIG. 29, the vibrating plate 22 is extended (flexed) inwardly and shown, causing the level of the treatment composition TC within the base cavity 64 to rise slightly, however a sufficient headspace HS exists within the base cavity 64 the mist generator assembly 400 is not flooded and it operates normally.

FIGS. 30, 31 and 32 depict a mist generator assembly 400 generally as described with reference to FIG. 22, as well as with reference to FIGS. 27, 28 and 29. Similarly to those figures, the vibrating plate 22 is depicted in three different states but oscillates at a different frequency as shown in prior FIGS. 27, 28 and 29. Similarly thereto however, although the operating characteristics of the plate 22 differs, e.g. vibrates or oscillates differently, still in each configuration there remains a sufficient headspace HS within the base cavity 64 the mist generator assembly 400 is not flooded and it operates normally. In the embodiments of FIGS. 30, 31 and 32 the different oscillatory pattern of the vibrating plate 22 provided different pattern of delivery of the mist of the treatment composition TM.

FIGS. 33, 34, 35, 36, and 37 respectively depict the mist generator assembly 400 according to FIG. 22 in five different orientations or, namely in FIG. 33 in an upright vertical orientation, viz., 90° upward with respects to the horizontal, in FIG. 34 in an upwardly inclined orientation, viz., at approximately 45° with respect to the horizontal, in FIG. 35 in a horizontal orientation, viz., at 0° with respect to the horizontal, in FIG. 36 in a downwardly inclined orientation, viz. at approximately 45° below, and with respect to the horizontal, and finally in FIG. 37, in a downward vertical orientation, 90° below and with respect to the horizontal, each orientation is indicated by the respective line labeled "H" in the figures. Turning first to FIG. 33, as visible there from the treatment composition TC is pumped through the fluid conduit 30 into the mist generator assembly 400. Part of the treatment composition TC occupies part of the base cavity 64, while the remainder of the base cavity 64 comprises the headspace HS above the treatment composition TC. As the vibrating plate 22 operates, the mist of the treatment composition TM is formed and exits in a horizontal direction away from the mist generator assembly 400. Any excess treatment composition TC from within the base cavity 64 may exit (in the direction of the arrow labeled "OF") outwardly from the mist generator assembly 400 via the overflow conduit 46C. In FIG. 34, in this inclined orientation, treatment composition TC pumped through the fluid conduit 30 and present within the base cavity 64 occupies part of the base cavity 64, the remaining part of which is unoccupied forms the headspace HS above the treatment composition TC. As a vibrating plate 22 operates, a mist of the treatment composition TM is formed and exits the mist generator assembly 400 downward angled direction. Any excess treatment composition TC from within the base cavity 64 may exit the mist generator assembly 400 in the direction of the arrow labeled "OF" via the overflow conduit 46C. Turning now to FIG. 35, in this horizontal orientation, treatment composition TC pumped through the fluid conduit 30 and present within the base cavity 64 occupies part of the base cavity 64, the remaining part of which is unoccupied forms the headspace HS above the treatment composition TC. As a vibrating plate 22 operates, a mist of the treatment composition TM is formed and exits the mist generator assembly 400 downwardly. Any excess treatment composition TC from within the base cavity 64 may exit the mist generator assembly 400 in the direction of the arrow labeled "OF" via the overflow conduit 46C. Considering now FIG. 36, in this downwardly inclined orientation, treatment composition TC pumped through the fluid conduit 30 and present within the base cavity 64 occupies part of the base cavity 64, the remaining part of which is unoccupied forms the headspace HS above the treatment composition TC. As a vibrating plate 22 operates, a mist of the treatment composition TM is formed and exits the mist generator assembly 400 downwardly in an angled direction. Any excess treatment composition TC from within the base cavity 64 may exit the mist generator assembly 400 via the overflow conduit 46C. Now considering FIG. 37, in this downward vertical orientation, treatment composition TC pumped through the fluid conduit 30 and present within the base cavity 64 occupies part of the base cavity 64, the remaining part of which is unoccupied forms the headspace HS above the treatment composition TC. As a vibrating plate 22 operates, a mist of the treatment composition TM is formed and exits the mist generator assembly 400 in a horizontal direction. Any excess treatment composition TC from within the base cavity 64 may exit the mist generator assembly 400 via the overflow conduit 46C.

As can now be appreciated following a consideration of the foregoing drawings, the embodiment of the mist generator assembly 400 is relatively insensitive as to its orientation with respect to the environment, and/or with respect to the surface to be treated utilizing a device of the invention, as regardless of its orientation it will remain operative as long as a sufficient quantity of treatment composition TC is present within the interior of the mist generator assembly 400, or namely within the base cavity 64 such that while the vibrating plate 22 of the mist generator means 20 operates, a treatment mist TM can be formed and delivered from the mist generator assembly 400. The provision of the overflow conduit 46C in fluid communication with the base cavity 64, here via the trough 46T (although trough is not required) permits for means of also ensuring that the base cavity 64 is not flooded with excess treatment composition TC. The egress of any excess treatment composition TC may be controlled by the placement of the overflow conduit 46C, and indeed a plurality of overflow conduits 46C is foreseen. Furthermore, the rate of egress of treatment composition from an overflow conduit 46C may be controlled such as by providing a downstream valve, or other flow controlling or flow directing means (not shown). In such a manner, the controller (not shown) and/or pump (not shown) may be used to control the volumetric supply rate of the treatment composition via the fluid conduit 30, and/or the volumetric egress rate of overflow treatment composition exiting the mist generator assembly 400 such that on the one hand a sufficient quantity of treatment composition TC is present within the base cavity 64 and in contact with the vibrating plate 22 when the mist generator 20 operates, and at the same time an excessive amount of the treatment composition TC is not present within the base cavity 64 such that the undesired flooding of the mist generator assembly 400 and especially the mist generator 20 is avoided irregardless of the orientation of the mist generator means with respect to the horizontal. In such a manner, and providing such an embodiment of a mist generator means 400 and a wide latitude in the control of the direction of the mist of the treatment composition TM can be provided in devices of the invention and methods of the invention. Similarly, it is to be understood that such a benefit may also be provided with a mist generator assembly 400 which does not include an overflow conduit, such as the embodiment of the mist generator assembly 400 In such an embodiment, careful control of the ingress or supply of treatment composition TC is required in order to provide optimal operating characteristics, and minimize the likelihood of flooding.

FIGS. 20A 38, 39 and 40 illustrated several alternative views a preferred embodiment of a mist generator assembly 400 similar in most respects to the embodiment of FIG. 22. As depicted in the cross-sectional view presented in FIG. 38, the first body element 40A has mounted therein a mist generator means 20 which abuts against a base cavity 64. A supply fluid conduit 30 extends into the base cavity 64, and an overflow conduit 46C is also in fluid communication with the base cavity 64 via a part of the trough 46T. The mist generator means 20 is in a sealed tight connection with the first body element 40A and is retained therein by a pair of extending lobes 402 which are made of a flexible elastomeric material and, in the embodiment depicted the entire first body element 40A is formed of a flexible or elastomeric material, here are preferably formed of a rubber-like material, which may for example be a rubber, a silicone material, silicon elastomer, or for that matter any other elastomeric material which provides both structural, and fluid sealing surfaces which can be used to both retain, to form a liquid tight seal between the first body element 40A and the mist generator means 20. FIG. 39 illustrates the mist generator assembly 400 and its elements in a perspective view; also visible is a wire cavity "WP" within which the wires 40 (or other electrical current carrying conductors) connected to the mist generator means 20 may exit the mist generator assembly 400. FIG. 40 depicts the same as generator assembly 400 in a plan view.

FIG. 41 illustrates a representational view of a pair of mist generator assemblies 400, preferably one or more of the mist generator assemblies according to FIGS. 22, and/or 38 affixed to a mounting plate "MP" forming part of the device of the invention. In this figure is shown a pair of fluid control means 90, which may be any device which may impart control over the quantity or quality of the fluid treatment composition passing outwardly from a reservoir 80. The reservoir 80 may be a refillable reservoir, a removable refill package, a cartridge, or any other vessel for containing a quantity of the treatment composition TC. In the depicted embodiment the fluid control means nine your most conveniently a pair of pumps, especially preferably a pair of piezoelectric pumps which can be operated by and controlled by the controller means (not shown) in order to supply controlled amounts of the treatment composition TC to each of the mist generator assemblies 400. The amount of treatment composition supply to each of the mist generator assemblies 400 is not necessarily the same, but can vary in response to input from the controller but, in many operations or operating modes such will be essentially identical. The controller (not shown) operates the fluid control means 90, and did the mist generator assemblies 400 in order to generate plumes of mist of the treatment composition TM which exit the mist generator assemblies 400 via horns or other perforations PP within the mounting plates PM.

FIG. 42 illustrates one embodiment of a device 1 according to the present invention. The device 1 includes a first assembly 120 which includes a quantity of fluid treatment composition TC within a reservoir 80, a mist generator 20 submerged within the treatment composition TC which is attached to a controller means 140 by means of an intermediate wire or wires at 150, over which are also transmitted the power required to drive the mist generator 20. The first assembly 120 is openable via a top cover 122, which has passing therethrough two connector ports, an airflow inlet connector port 123 and a mist output connector port 124. While not depicted in the figure, but represented to by the arrow labeled "G" is an airflow generator means which provides a stream of a gas, preferably air via the airflow tube 123A which generates an elevated pressure within the interior of the vessel 80. The treatment composition in the form of a mist TM present within the vessel 80 is forced out via the mist tube 124A which directs it to the control handle 160 or control "wand", which has a flow directing nozzle 162 at its a distal end 161 from which the mist of the treatment composition TM emanates. The control handle 160 is gripped by a person and as the mist tube 124A is flexible and separate from the first assembly 120 it can be conveniently used to deliver a quantity of the mist of the treatment composition TM to a desired location.

FIG. 43 illustrates an alternative embodiment of a first assembly 120, which is a self-contained, in that the controller means, power supply source, and airflow generator are contained in the housing 129 forming a part of the first assembly 120, for example, a battery powered blower or fan may be used in providing sufficient pressure within the interior of the reservoir 80 so to cause the flow of the mist of the treatment composition through the mist tube 124A. Such a self-contained first assembly provides for a more portable device 1 according to the invention.

FIG. 44 depicts a device according to the invention which includes the first assembly 120 as generally depicted with reference to FIG. 45, to which is attached a flexible strap 128 which can be used to hang the first assembly 120 from a body part such as a shoulder. The device 1 also includes a control handle 160 connected to the first assembly 120 by an intermediate, flexible mist tube 124A, from which the treatment composition in the form of the mist can be delivered. A control button 163 they be used to control the release of the treatment composition from the flow directing nozzle 162.

FIG. 45 illustrates a further embodiment of a device 1 according to the invention wherein in the first assembly 120 is provided on a wheeled cart 125, such as may be desired when a large amount of the treatment composition in the form of the mist is required to be dispensed. The depicted embodiment is similar in most respects to that described on FIG. 44; the figure also illustrates the manner in which a "soft surface" can be treated, here illustrated as a hanging curtain TS. In use, a user merely directs the release of the aerosolized treatment composition, namely the treatment mist TM from the flow directing nozzle 162 of the control handle 160.

FIG. 46 illustrates in a cross-sectional view a simple embodiment of a control handle 160 or control "wand" according to the prior embodiment of FIGS. 24 and 25. In this view, the mist tube 124 enters through the proximal end 164 of the control handle 160, and extends to a release valve 163A which can be manually controlled by the control button 163, so that when the release valve 163A is in an "open" condition, the mist of the treatment composition flows through a nozzle tube 124B and to the flow directing nozzle 162, from whence the aerosolized or mist of the treatment composition exits. Manual gripping of the control handle 160 they be improved by providing a number of gripping the recesses 164B for cradling one or more fingers of a human operator holding and operating in the control handle 160.

FIG. 47 illustrates a cross-sectional view of a further embodiment of a device 1 in a self-contained and portable assembly. A shaped housing 170 includes at one end a flow directing nozzle 162 which is in communication with the interior of the housing 170, and at the opposite end includes a removable cover 171 through which a reservoir 80 and a power supply source 190, here one or more electrical batteries, may be inserted within the shaped housing 170. Advantageously, an air intake grille 172 is also present in the housing 170 and preferably it is formed at or near the opposite end of the flow directing nozzle. Within the interior of the housing 170 is also located a control circuit means (not shown), and airflow generator, here in the form a blower 200 which is driven by a small electrical motor 202 which is suitably mechanically coupled to the drive shaft (not shown) of the blower 200. A supply means 70 extends outwardly from the reservoir 80 and is sufficiently proximate to a mist generator 20 such that, upon activation thereof a mist TM of aerosolized treatment composition present within the interior of the reservoir is generated. To facilitate the movement and delivery of the airborne mist of the treatment composition the blower 200 directs a stream of moving air from its outlet 203 and inducing its to flow out from the flow directing nozzle 162 of the device 1. Such a device is portable, and compact, and also practical as frequently one or more treatment operations can be performed without requiring either replenishment or replacement of the reservoir 80, and or replacement or recharging of the one or more batteries 190. Furthermore, as the generation of a mist of the treatment composition is essentially nearly instantaneous with the activation of the mist generator 20, power can be spared in-between surface treatment operations as control button 163 which energizes the control means and consequently the blower 200 and the mist generator 20 need only be used to activate and operate the device 1 when actually treating a surface.

FIGS. 48, 49, 50, 53 illustrate views of a preferred embodiment of a device 1 in a self-contained and portable embodiment. A shaped housing 170 includes a plurality of flow directing nozzles 162 which extend through a mounting plate MP forming part of the housing 170, behind each of which nozzles 162 is mounted three mist generating assemblies 400 which are generally as described with reference to FIGS. 38, 39 and 40. Also illustrated both mounted and unmounted in the device 1 is a cartridge shaped reservoir 80 which is fitted into the housing 170. The device 1 includes a slideable switch 163A which may be operated by a user to control the operation of the device 1. Although not illustrated in the figure, within the housing is also present at least a power supply source, preferably one or more electrical batteries, (rechargeable, or non-rechargeable), control circuit means (not shown), and at least one, but may also be two or more pumps and necessary tubing or other fluid conduits in order to provide for supply of the treatment composition present within the cartridge shaped reservoir 80 to be supplied to each of the mist generator means 20 of each of the three mist generating assemblies 400 in response to appropriate control signals from the control circuit means which concurrently also operates the mist generator 20 and the one or more pumps, preferably piezoelectric diaphragm pumps such as those presently commercially available from Bartels Mikrotechnik GmbH. In less preferred embodiments the mist generator assemblies 400 may be any other mist generating assembly 400 which may operate in accordance to the principles outlined in one or more of FIGS. 33, 34, 35, 36 and 37. The use of one or more, here three, mist generator assemblies 400 permits the device 1 may be operated in a variety of inclinations or orientations with respect to the horizontal as previously described. Such also dispenses for any need of an airflow generator means to increase the flowrate of the mist of the treatment composition as the mist generator means 20 dispense the mist of the treatment composition TM directly outwardly from the mounting plate MP. Accordingly in preferred embodiments devices of the invention exclude such an airflow generator means.

FIG. 51 illustrates a part of the device 1 depicted in figures FIGS. 48, 49, 50, 53. FIG. 51 illustrates and plan view the mounting plate MP as viewed from within the interior of the device 1. As visible thereon, three mist generating assemblies 400 are arrayed in a generally linear arrangement are a fixed or otherwise mounted to the mounting plate MP.

FIG. 52 illustrates a cross-sectional view of the device according to FIGS. 48, 49, 50, 53 and 51 according to line "DD" of FIG. 53. as is visible thereon, the mounting plate MP is positioned on the underside of the device 1 and op. cit. the handle 160 which is inclined with respect thereto. The handle 160 is grippable and suited to be grasped by the hand of a user. The three mist generator assemblies 400 are arranged such that treatment composition generated therefrom pass through the mounting plate MP and the flow directing nozzles 162 formed as part thereof; here the flow directing nozzles are simple orifices or holes passing therethrough with either straight, or slightly tapered sidewalls to impart a "horn-like" shape. As has is understood from this patient the drawing, the mist generator means 20 or essentially virtually adjacent to the flow directing nozzles 162 which dispenses with the need for an airflow generating device. While not visible in this view, is to be understood that each of the mist generator assemblies 400 are connected to further elements of the device including but not limited to a power supply source, preferably one or more electrical batteries, a control circuit means, and at least one pump and necessary tubing or other fluid conduits in order to provide for supply of the treatment composition present within the cartridge shaped reservoir 80 to be supplied to each of the mist generator means 20 each of the three mist generating assemblies 400 in response to appropriate control signals from the control circuit means which concurrently also operates the mist generator 20 and the one or more pumps.

While not illustrated with respect to the preferred embodiment of FIGS. 48, 49, 50, 53, 51 and 52, the device 1 may include an openable cover part which can be hinged, or removable and replaceable, such as to permit access to the interior of the device 1 particularly in a location wherein replaceable batteries may be positioned, such that their removal and replacement with fresh batteries can be facilitated. For example part of the handle 160 may include such an openable cover part, allowing access to the interior especially were one or more batteries are present within the handle. In place of the slideable switch 163A, other types of switches may be included as well as a plurality of switches or sliders or other signal input means may also be provided. Such switches may be movable between two or more positions, and in its most simplest form operates only as an "on" and "off" switch, but preferably includes a least one or more intermediate settings. The one or more intermediate settings can be used to establish various operating parameters of the device 1, such as controlling the rate of delivery of the mist of the treatment composition, timer means to automatically engaged, and disengage operation of the device 1 at one or more preselected intervals of time and thereby providing for unattended operation of the device 1, or other operating parameters. The device 1 may also include one or more status indicator means, which provide visual feedback to the user of the device. Bonlimiting examples include light emitting diodes, or a small LCD or LED panel which are properly displays symbols relevance to the operating status of the device, such as pictographs, icons, written words, numerical indicators, and the like. However, the status indicator means can be any visually discernible, audio discernible, tactile discernible indicators which provide information regarding the status of the device including the operating status of the device 1 to a user.

Such a device 1 is portable, compact, and also practical, as frequently one or more treatment operations can be performed without requiring either replenishment or replacement of the reservoir 80, and or replacement or recharging of the one or more batteries. Furthermore, as the generation of a mist of the treatment composition is essentially nearly instantaneous with the activation of the mist generator 20, and the direction of the directional delivery of the mist of the treatment composition may vary widely, the device 1 is both effective and convenient in use.

FIG. 54 depicts a simplified manner of treating a textile surface, here the upholstered surface of a chair TU. A device according to the invention 1, e.g., the embodiment according to FIGS. 48, 49, 50, 53, 51 and 52 is operated such that the aerosolized treatment composition, namely the mist TM is used to contact the textile surface by appropriate placement of the device 1 while it operates. The mist of the treatment composition TM not only contacts the surface of the textile, but may also penetrate into and through the textile to provide a technical benefit, e.g., cleaning, sanitizing, disinfecting, fragrancing, deodorizing, odor neutralizing, anti-allergen, therapeutic, and/or other technical benefit.

FIG. 55 depicts a simplified manner of treating a hard surface, here a tiled ceramic surface, e.g. a kitchen countertop, a shower stall, a bathtub surround, or a flooring or wall surface. A device 1 according to the invention, e.g., the embodiment according to FIGS. 48, 49, 50, 53, 51 and 52 is operated such that the aerosolized treatment composition, namely the mist of the treatment composition TM is used to contact the hard surface by appropriate placement of the device 1 in proximity to the hard surface while it operates. Due to the airborne nature of the mist of the treatment composition TM, it typically remains airborne or floats for at least several seconds before evenly depositing upon surfaces in the locus in which it has been applied.

While not illustrated it is contemplated that the device of the invention may be used to treat the interior and contents of a clothes washing machine as well as a clothes dryer and the device may be used prior to a clothes washing or drying cycle, during a clothes washing or drying cycle, or after a clothes washing or drying cycle to release a treatment mist TM therefrom.

While not illustrated it is contemplated that the device of the invention may be used to treat textiles and garments, especially stains on clothing and garments particularly localized stains. Such a treatment to prior to a clothes washing or drying cycle, during a clothes washing or drying cycle, or after a clothes washing or drying cycle. The treatment of such textiles and garments may provide a cleaning benefit, a fragrancing benefit, in order neutralizing benefit, or for that matter any other technical benefit as may be desired or necessary.

While not illustrated it is contemplated that the device of the invention may be used to treat cookware, dishware, serving ware, eating utensils, tableware, and the like. The device may be operated to dispense a mist of a treatment composition onto such articles at any desired time. One example, such a treatment may occur prior to subjecting cookware, dishware, serving ware, eating utensils, and/or tableware to a subsequent washing operation, especially subject to a wash operation in an automatic dishwashing machine. Another example, such a treatment may curse subsequent to a washing operation, and the device is used to provide a treatment benefit, e.g., a surface coating, a layer of a sanitizing or disinfecting composition, onto surfaces of cookware, dishware, serving ware, eating utensils, tableware.

While not illustrated it is contemplated that a device according to the invention may be installed within the interior of a ware washing machine, e.g. an automatic dishwashing machine, in order to dispense a mist of a treatment composition thereto during part of a dishwashing cycle. The device can be permanently fixed therein, or can be removably affixed thereto such as by means of a suitable mounting bracket such that it is removable by the user should the device require refilling the fresh quantity of the treatment composition TC, or for servicing. It is also contemplated that a device according to invention can be supplied as a unit which can be removably inserted by being laid within or suspended from a rack as is conventionally present in a dishwashing machine. The device can operate in response to an appropriate input, such as a sensor signal including but not limited to time, temperature, chemical composition of the wash liquor present within the ware washing machine such that in response thereto, the device operates in order to deliver a quantity of the mist of the treatment composition TM to the interior of the ware wash machine and its contents.

Similarly, while not illustrated the device according to the invention may be installed into the interior of a clothes washing machine and/or a clothes dryer. The device can be permanently affixed therein, or can be removably affixed thereto such as by means of a suitable mounting bracket such that it is removable by the user should the device require refilling the fresh quantity of the treatment composition TC, or for servicing. It is also contemplated that a device according to invention can be supplied as a unit which can be removably inserted within a clothes washing machine and/or a clothes dryer. The device can operate in response to an appropriate input, such as a sensor signal including but not limited to time, temperature, chemical composition of the wash liquor present within the ware washing machine such that in response thereto, the device operates in order to deliver a quantity of the mist of the treatment composition TM to the interior of the ware wash machine and its contents.

While not illustrated it is contemplated that the device of the invention may be used to treat the interior and contents of a shower stall. In such a process and device of the invention can be used to deliver a mist of the treatment composition TM wherein a user of the device manually brings the device into the interior of the shower stall and/or surfaces thereof and operates the device in order to dispense the treatment mist TM. Alternately, the device may be retained within the interior of the shower stall, e.g., suspended from a shower head or shower head supply pipe by a suitable hanger means, or may be adhered to a part of the shower stall by one or more suction or adhesive means wherein the device can be suitably mounted, preferably removably mountable in such a manner. The device may thereafter be preprogrammed, or manually operated as desired in order to release a quantity of the mist of the treatment composition TM in order to treat surfaces on the interior and contents of the shower stall. In one preferred embodiment, a timer means is included within the control circuitry in order to automatically initiate the operation of the device and its dispensing of the mist of treatment composition TM on a time-based periodic basis, or alternately made be cost operating response the receipt of a suitable signal. Optionally the device further includes an air-treatment means which provides an ancillary air treatment benefit.

While not illustrated it is also contemplated that the device of the invention may be used to treat the interior of a refuse container, such as a garbage can, or garbage bin whether such be lined or online. The device may be affixed, or suspended cry part of the waste receptacle, e.g., by means of a suitable hanger, such that a quantity of the mist treatment composition TM at least periodically is released into the interior of the waste receptacle, and/or in the near proximity of the waste receptacle. In one embodiment, the waste receptacle includes a movable lid and the device can be mounted thereupon. In another embodiment, the device is mounted by means of a hanger, such that the device is within the interior of the waste receptacle. In both of the foregoing embodiments the mist of the treatment composition TM is directed into the interior of the waste receptacle and then can be used to treat the refuse or other contents of the waste receptacle either on a time-based, periodic basis, in response to a signal of a signal means, and/or in response to a user input which may activate the device.

It is naturally to be understood that the embodiments discussed in the foregoing figures are by way of illustration and not by way of limitation. It is also to be clearly understood that various elements presented in the disclosed embodiments may be substituted in the place of like or similar elements in different embodiments. Particularly, it is foreseen in fact different forms of mist generators 20 can be substituted in different embodiments of devices 1 presented herein.

The invention claimed is:

1. A hand-holdable, portable device which, during operation, generates an aerosolized mist of a liquid hard surface treatment composition or a liquid soft surface treatment composition, or a liquid airspace treatment composition, which aerosolized mist imparts a technical benefit to treated surfaces, or airspaces which come into contact with the said aerosolized mist, the device comprising:
   a reservoir for the liquid treatment composition to be aerosolized,
   a mist generator assembly which comprises:
      a body element formed of an flexible or elastomeric material;
      a base cavity present within the body element;
      a supply fluid conduit in fluid communication within the base cavity;

an atomizing chamber within the body element;
an open end of the atomizing chamber; and,
a mist generator which includes a vibratable micro-perforated screen physically bonded to a piezoelectric actuator which mist generator means is mounted in a liquid, seal-tight manner within the mist generator assembly between the base cavity and the open end of the atomizing chamber the device further comprises a pump which operates to supply liquid treatment composition from the reservoir to the base cavity via the supply fluid conduit, the mist generator assembly being configured such that, during the operation of the device, liquid treatment composition is always in at least partial contact with the micro-perforated screen, the device further including means to ensure, such that during the operation of the device, a headspace is present above the liquid treatment composition within the fluid dispensing cavity, the device further comprising control means for operating the mist generator means, and optionally at least one flow directing nozzle, flow directing implement or flow directing orifice adapted to direct the flow of an aerosolized mist of the liquid treatment product generated by the mist generating means and towards a surface or into an airspace or both.

2. A method for the treatment of an airspace which method comprises the steps of:
providing a hand-holdable, portable device according to claim 1, and
operating the device to generate an aerosolized mist of the liquid treatment composition, which aerosolized mist contacts the airspace and provides a technical benefit thereto.

3. A method for the treatment of a dermal surface which method comprises the steps of:
providing a hand-holdable, portable device according to claim 1, and
operating the device to generate an aerosolized mist of the liquid treatment composition, which aerosolized mist contacts the dermal surface and provides a technical benefit thereto.

4. A method for the treatment of a hard surface or a soft surface which method comprises the steps of:
providing a hand-holdable, portable device according to claim 1 and operating the device to generate an aerosolized mist of the liquid treatment composition, which aerosolized mist contacts the hard surface or soft surface and provides a technical benefit thereto.

5. A device according to claim 1 which includes at least one flow directing nozzle.

6. A device according to claim 1, wherein the mist generator assembly further includes an overflow conduit in fluid communication within the base cavity.

7. A device according to claim 1, wherein the means to ensure a headspace includes means to control the amount of liquid treatment composition supply to the cavity.

8. A device according to claim 1, wherein the pump is a piezoelectric diaphragm pump.

9. A device according to claim 1, wherein the device further includes an air flow generation means to increase the flow rate of the aerosolized mist.

10. A device according to claim 1, wherein all component parts of the device are provided within a single housing unit which is configured to be hand-holdable and portable.

11. A device according to claim 1, which includes a handle which houses means to power the control means.

12. A device according to claim 1, wherein the reservoir is a refill unit.

13. A device according to claim 1, which includes two or more mist generator assemblies.

14. A device according to claim 13, wherein the two or more mist generator assemblies are supplied from the reservoir.

15. A hand-holdable, portable device which, during operation, generates an aerosolized mist of a liquid hard surface or soft surface treatment composition or, a liquid airspace treatment composition which liquid treatment composition imparts a technical benefit to treated surfaces or airspaces which come into contact with the said aerosolized mist, the device comprising:
a reservoir for the liquid treatment composition to be aerosolized,
a mist generator assembly which comprises:
a body element formed of an flexible or elastomeric material;
a base cavity present within the body element;
a supply fluid conduit in fluid communication within the base cavity;
an overflow conduit in fluid communication within the base cavity;
an atomizing chamber within the body element;
an open end of the atomizing chamber; and,
a mist generator which includes a vibratable micro-perforated screen physically bonded to a piezoelectric actuator which mist generator means is mounted in a liquid, seal-tight manner within the mist generator assembly between the base cavity and the open end of the atomizing chamber,
the device further comprising a pump which supplies liquid treatment composition from the reservoir via the supply fluid conduit to the base cavity, the mist generator assembly being configured such that during the operation of the device an aerosolized mist is generated only when the said liquid composition is in contact with the micro-perforated screen,
the device further comprising control means for operating the mist generator,
and optionally at least one flow directing nozzle, flow directing implement or flow directing orifice adapted to direct the flow of an aerosolized mist of the liquid treatment product generated by the mist generating means and towards a surface or into an airspace or both.

16. A device according to claim 15, wherein the device further includes:
means to ensure, such that during the operation of the device, a headspace is present above the liquid treatment composition within the base cavity.

17. A device according to claim 1 which contains a liquid inanimate hard surface treatment composition or a liquid inanimate soft surface treatment composition which comprises a surfactant.

18. A device according to claim 1 which contains a liquid air treatment composition or a liquid airspace treatment composition which comprises a fragrance.

* * * * *